United States Patent
Haselton et al.

(10) Patent No.: US 10,968,475 B2
(45) Date of Patent: Apr. 6, 2021

(54) MONITORING AND ANALYSIS OF NUCLEIC ACID HYBRIDIZATION STATE AND AMPLIFICATION USING L-DNA

(71) Applicant: VANDERBILT UNIVERSITY, Nashville, TN (US)

(72) Inventors: Frederick R. Haselton, Nashville, TN (US); Nicholas M. Adams, Nashville, TN (US); Steven J. Simmons, Unionville, TN (US); Elliott P. Dawson, Murfreesboro, TN (US)

(73) Assignees: VANDERBILT UNIVERSITY, Nashville, TN (US); BIOVENTURES, INC., Murfreesboro, TN (US)

( * ) Notice: Subject to any disclaimer, the term of this patent is extended or adjusted under 35 U.S.C. 154(b) by 108 days.

(21) Appl. No.: 15/571,153

(22) PCT Filed: May 2, 2016

(86) PCT No.: PCT/US2016/030411
§ 371 (c)(1),
(2) Date: Nov. 1, 2017

(87) PCT Pub. No.: WO2016/179090
PCT Pub. Date: Nov. 10, 2016

(65) Prior Publication Data
US 2018/0171393 A1  Jun. 21, 2018

Related U.S. Application Data

(60) Provisional application No. 62/155,491, filed on May 1, 2015.

(51) Int. Cl.
*C12Q 1/6818* (2018.01)
*C12Q 1/68* (2018.01)
(Continued)

(52) U.S. Cl.
CPC .............. *C12Q 1/6818* (2013.01); *B01L 7/52* (2013.01); *C12Q 1/68* (2013.01); *C12Q 1/686* (2013.01);
(Continued)

(58) Field of Classification Search
None
See application file for complete search history.

(56) References Cited

U.S. PATENT DOCUMENTS

| 4,996,143 A | 2/1991 | Heller et al. |
| 5,188,934 A | 2/1993 | Menchen et al. |

(Continued)

FOREIGN PATENT DOCUMENTS

WO  2012/037531 A1  3/2012

OTHER PUBLICATIONS

Kim et al., "Superior structure stability and selectivity of hairpin nucleic acid probes with an L-DNA stem," Nucleic Acids Research, vol. 35, No. 21, pp. 7279-7287. (Year: 2007).*

(Continued)

*Primary Examiner* — Young J Kim
(74) *Attorney, Agent, or Firm* — Tarolli, Sundheim, Covell & Tummino LLP

(57) ABSTRACT

Systems, methods, and compositions for monitoring and analyzing nucleic acid hybridization state using L-DNA probes are described. The methods include adding L-DNA probes that can be fluorescently detected to a system including D-DNA. The L-DNA probes include primer, target, and antisense nucleotide sequences, and fluorescent dye compounds. The L-DNA probes are particularly useful for monitoring and analyzing various parameters during DNA amplification using the polymerase chain reaction.

6 Claims, 19 Drawing Sheets

Specification includes a Sequence Listing.

(51) Int. Cl.
   *B01L 7/00* (2006.01)
   *C12Q 1/686* (2018.01)
(52) U.S. Cl.
   CPC .... *C12N 2310/122* (2013.01); *C12N 2310/32* (2013.01); *C12Q 2525/101* (2013.01); *C12Q 2525/113* (2013.01); *C12Q 2531/113* (2013.01); *C12Q 2537/143* (2013.01); *C12Q 2561/113* (2013.01); *Y02A 50/30* (2018.01)

(56) References Cited

U.S. PATENT DOCUMENTS

| | | | |
|---|---|---|---|
| 5,532,129 | A | 7/1996 | Heller |
| 5,565,322 | A | 10/1996 | Heller |
| 2004/0086879 | A1* | 5/2004 | Li ................. C12Q 1/6818 435/6.11 |
| 2006/0029965 | A1 | 2/2006 | Wittwer et al. |
| 2007/0059690 | A1* | 3/2007 | Islam ............... C12Q 1/6818 435/6.12 |
| 2013/0071880 | A1* | 3/2013 | Corbett ............. C12Q 1/686 435/91.2 |
| 2013/0260368 | A1 | 10/2013 | Pollner et al. |

OTHER PUBLICATIONS

Hayashi et al. "Application of L-DNA as a Molecular Tag", Nucleic Acids Symposium Series, No. 49, pp. 261-262, Sep. 1, 2008.
Hauser et al. "Utilising the Left-Helical Conformation of L-DNA for Analysing Different Marker Types on a Single Universal Microarray Platform", Nucleic Acids Research, vol. 34, No. 18, pp. 5101-5111, Sep. 20, 2006.
Hosoda et al. "A Novel Sequence-Specific RNA Quantification Method Using Nicking Endonuclease, Dual-Labeled Fluorescent DNA Probe, and Conformation-Interchangeable Oligo-DNA", RNA, vol. 14, pp. 584-592, Jan. 29, 2008.
International Search Report dated Jul. 24, 2016 for corresponding International Application No. PCT/US2016/030411.
Ke et al. (2012) L-DNA Molecular Beacon: A Safe, Stable, and Accurate Intracellular Nano-thermometer for Temperature Sensing in Living Cells. Journal of the American Chemical Society 134, pp. 18908-18911.
Kim et al. "Superior structure stability and selectivity of hairpin nucleic acid probes with an L-DNA stem", Nucleic Acids Research, vol. 35, pp. 7279-7287, Oct. 24, 2007.
Saunders et al. "Interlaboratory study on thermal cycler performance in controlled PCR and random amplified polymorphic DNA analyses", Clinical Chemistry, vol. 47, pp. 47-55, 2011.
Sharma et al. "A novel method for whole blood PCR without pretreatment", Gene vol. 501, issue 1, pp. 85-88, Jun. 2012.
Rahimi et al. "Direct urine polymerase chain reaction for chlamydia and gonorrhoea: a simple means of bringing high-throughput rapid testing to remote settings", Sexual health vol. 10, pp. 299-304, 2013.
Wetmur, J. G. "Hybridization and Renaturation Kinetics of Nucleic-Acids", Annual Review of Biophysics and Bioengineering, vol. 5, pp. 337-361, 1976.
Williams et al. "Bioactive and nuclease-resistant L-DNA ligand of vasopressin", Proceedings of the National Academy of Sciences of the United States of America vol. 94, pp. 11285-11290, Oct. 1997.
Tichopad et al. "Standardized determination of real-time PCR efficiency from a single reaction set-up", Nucleic Acids Research, vol. 31, No. 20, e122, 2003.
Sur et al. "Immiscible phase nucleic acid purification eliminates PCR inhibitors with a single pass of paramagnetic particles through a hydrophobic liquid", The Journal of Molecular Diagnostics : JMD vol. 12, No. 5, pp. 620-628, Sep. 5, 2010.
Aggarwal et al. "Use of amplified Mycobacterium tuberculosis direct test (Gen-probe Inc., San Diego, CA, USA) in the diagnosis of tubercular synovitis and early arthritis of knee joint", Indian Journal of Orthopaedics, vol. 46, pp. 531-535, Sep. 2012.
Sanford et al. "Monitoring Temperature by Fluorescence During PCR and Melting Analysis", Journal of Molecular Diagnostics vol. 14, pp. 743-743, 2012.
Ozaki et al. "The Estimation of Distances Between Specific Backbone-Labeled Sites in DNA Using Fluorscence Resonance Energy Transfer", Nucleic Acids Research vol. 20, No. 19, pp. 5205-5214, Sep. 1992.
Bagwell et al. "A New Homogeneous Assay System for Specific Nucleic Acid Sequences: Poly-dA and Poly-A Detection", Nucleic Acids Research vol. 22, No. 12, pp. 2424-2425, May 1994.
Cardullo et al. "Detection of Nucleic Acid Hybridization by NonRadiative Fluorescence Resonance Energy Transfer", Proceedings of the National Academy of Sciences of the United States of America vol. 85, pp. 8790-8794, Dec. 1988.
Bengtsson et al., "A New Minor Groove Binding Asymmetric Cyanine Reporter Dye for Real-Time PCR", Nucleic Acids Research vol. 31, No. 8, e45, Feb. 2003.
Wittwer et al. "Continuous Fluorescence Monitoring of Rapid Cycle DNA Amplification", Biotechniques, Jan. 1997.
Nygren et al., "The Interactions Between the Fluorescent Dye Thiazole Orange and DNA", Biopolymers, Jul. 1998.
Hayashi, Gosuke, et al. "Detection of l-DNA-Tagged PCR Products by Surface Plasmon Resonance Imaging." ChemBioChem 8.2 (2007): 169-171.
Hayashi, Gosuke, Masaki Hagihara, and Kazuhiko Nakatani. "Genotyping by allele-specific L-DNA-tagged PCR." Journal of biotechnology 135.2 (2008): 157-160.
Adams, Nicholas M., et al. "Adaptive PCR Based on Hybridization Sensing of Mirror-Image l-DNA." Analytical chemsitry 89.1 (2016): 728-735.

* cited by examiner

A

B

Low Temperature Probes    High Temperature Probes intercalating dye intercalating dye

SEQUENCE LISTING

<160> NUMBER OF SEQ ID NOS: 10

<210> SEQ ID NO 1
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ctttgtcacc gacgcctac                                                 19

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
tcgaggacca tggaggtg                                                  18

<210> SEQ ID NO 3
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ctttgtcacc gacgcctacg tcgcaggatc ctgggctggc gggtcgcttc cacgatggcc    60
acctccatgg tcctcga                                                   77

<210> SEQ ID NO 4
<211> LENGTH: 77
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tcgaggacca tggaggtggc catcgtggaa gcgacccgcc agcccaggat cctgcgacgt    60
aggcgtcggt gacaaag                                                   77

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
tacatccgtg aggtgaatgt g                                              21

<210> SEQ ID NO 6
<211> LENGTH: 21

```
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
cacattcacc tcacggatgt a                                             21

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 7
tacatccgtg aggtgaatgt ggtgaagt                                      28

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
acttcaccac attcacctca cggatgta                                      28

<210> SEQ ID NO 9
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
gtactcaatg attgcgcaag gttttttttc cttgcgcaat cattgagtac              50

<210> SEQ ID NO 10
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
caagactatg attgccctac gttttttttc gtagggcaat catagtcttg              50
```

MONITORING AND ANALYSIS OF NUCLEIC ACID HYBRIDIZATION STATE AND AMPLIFICATION USING L-DNA

CONTINUING APPLICATION DATA

This application claims the benefit of U.S. Provisional Application Ser. No. 62/155,491, filed May 1, 2015, which is incorporated by reference herein.

SEQUENCE LISTING

The instant application contains a Sequence Listing which has been submitted electronically in ASCII format and is hereby incorporated by reference in its entirety. Said ASCII copy, created on May 24, 2016, is named VU-024403 WO ORD_SL.txt and is 2,755 bytes in size.

BACKGROUND OF THE INVENTION

Because of its high sensitivity, polymerase chain reaction (PCR) is the gold standard for the diagnosis of many infectious diseases, but it is generally only implemented in well-equipped laboratory facilities. One of the major roadblocks for expanding PCR to point-of-care markets is the lack of simple, robust, single tube PCR designs which preserve its laboratory-based high sensitivity and specificity One of the major impediments to simple, robust, and single tube PCR is that the amplification reaction only occurs within a narrow range of thermal and chemical conditions. Point-of-care settings, including walk-in clinics, rural health outposts, and outbreak surveillance by mobile response units, generally lack the stringent sample preparation and controlled environmental requirements available in centralized laboratory facilities, where samples are batched and PCR performed with a series of standards and control reactions. A fundamental limitation with all current PCR designs is that thermal cycling is controlled by pre-determined indirect temperature measurements, yet the PCR product melting step and, more importantly, the primer annealing step, do not always occur at the programmed temperatures. Individual reaction conditions, ambient temperatures, and thermal calibrations create disparities between the expected hybridization state of the product or primers and the actual state. These disparities are exacerbated in diagnostic settings that are less equipped to precisely control environmental conditions and sample contents, leading to PCR failure, i.e., false negatives in diagnostic applications.

Major changes are needed to better match PCR designs to settings that lack laboratory infrastructure. One mismatch is that point-of-care settings, especially where resources are limited, have a much lower throughput than central laboratories. In central laboratories PCR is generally performed only after a sufficient number of samples have been collected, typically in batches that fill 96-well plates. One major reason for this is to reduce costs, because interpreting PCR results requires additional controls and standards to be run in parallel to identify false negatives and false positives, which is cost prohibitive for individual samples. The need for these additional validating reactions is partly due to PCR's sensitivity to variation in ambient temperature and reaction contents, which can vary widely at the point-of-care or in laboratory settings. This creates the requirements of maintaining consistent ambient laboratory conditions, instrument calibrations, and technical training, each of which is difficult to maintain in point-of-care settings. Even in the best laboratories, the ultra-sensitivity of PCR to reaction conditions requires that every DNA target and primer set be optimized for the lab's PCR instrumentation to determine the appropriate reaction conditions, such as temperature and reaction times and salt concentrations, which must then be precisely maintained in all subsequent laboratory reactions. Saunders et al., Clinical chemistry 47, 47-55 (2001).

In diagnostic applications, reaction contents are of particular concern as a source for false negatives. PCR diagnostic reactions do not work without the careful separation of the target DNA from other components in the patient sample matrix. Current methods are mostly based on removal of interferents by phenol-chloroform partitioning or by solid-phase extraction of DNA usually to silica. In settings that lack trained personnel, simpler methods are preferred, such as preparations that enable PCR directly in a sample matrix. Sharma et al., Gene 501, 85-88 (2012); Rahimi et al., Sexual health 10, 299-304 (2013). However, because of patient-to-patient variation, the salt levels, pH, and other components of the reaction are not predictable and can alter the annealing and melt characteristics of DNA. Wetmur, J. G., Annual Review of Biophysics and Bioengineering 5, 337-361 (1976). This can lead to PCR failure and false negatives in PCR diagnostic applications. There is a great need for more robust PCR designs that compensate for errors in sample preparation, that do not require calibration and maintenance, and that tolerate the variability that might be expected with inexperienced users in settings or encountered as a consequence of simpler sample preparation designs.

SUMMARY OF THE INVENTION

The inventors have developed a fundamentally different method of monitoring and analyzing nucleic acid hybridization state which can be used to provide a new PCR design, referred to herein as hybridization-triggered PCR (HT-PCR), that provides a method to directly monitor the key hybridization events of the reaction by including fluorescently-labeled synthetic surrogates of the primers and product in the PCR reaction. See FIG. 1. A major advantage of this approach is that it enables hybridization-triggered heating and cooling without the need to know reaction temperatures and times. Thus the instrument dynamically self-calibrates for unpredictable thermal and chemical variations. A second major advantage is that the L-DNA surrogates of the PCR product can be used as controls for reagent rehydration, sample preparation, instrument performance, diagnostic threshold, and correct product formation, enabling well-controlled single-tube analysis of DNA. The design alters the way PCR cyclic amplification is monitored and controlled and results in a PCR implementation more suitable for underserved point-of-care markets.

It is to be understood that both the foregoing general description and the following detailed description are exemplary and explanatory only and are not restrictive of the invention, as claimed.

BRIEF DESCRIPTION OF THE FIGURES

FIG. 3A illustrates a fluorescence quencher design and FIG. 3B illustrates a design that incorporates FRET and quenchers. L-DNA analogs of the PCR products and a primer are labeled with fluorophores (5'-HEX on product strand, 5' Texas Red on primer strand) and a quencher (3' BHQ2 on the other product strand) to indicate product melting and primer annealing. The derivatives of these optical profiles identify key moments for temperature-independent switching between heating and cooling (i.e., cool once products melt and heat once primers anneal).

FIGS. 24A-43C provide graphs showing the effect of dye and quenchers on melting temperature. (A) shows the run data. (B) shows the melt curve. (C) shows the melt peaks, where Thermo62_FWD_unlabeled/REV_Unlableled=71° C.; and Thermo69_FWD_Unlabeled/REV_Unlabeled=75° C.

DETAILED DESCRIPTION OF THE INVENTION

Figure 1:
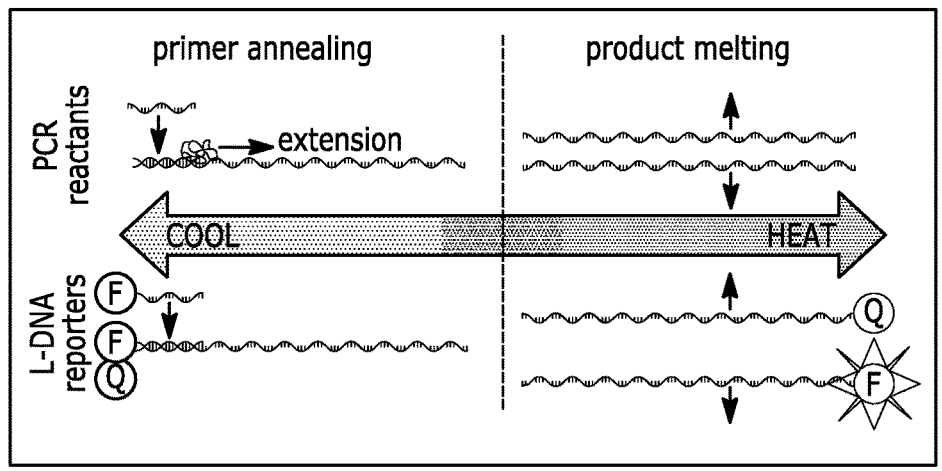
FIG. 1 provides an illustration of two-step PCR containing L-DNA probes (bottom) as surrogates for monitoring the hybridization state of PCR reactants (top) to control thermal cycling independent of temperature and time.

Unless otherwise defined, all technical and scientific terms used herein have the same meaning as commonly understood by one of ordinary skill in the art to which this invention belongs. The terminology used in the description of the invention herein is for describing particular embodiments only and is not intended to be limiting of the invention.

Definitions

As used in the description of the invention and the appended claims, the singular forms "a," "an," and "the" are intended to include the plural forms as well, unless the context clearly indicates otherwise. In addition, the recitations of numerical ranges by endpoints include all numbers subsumed within that range (e.g., 1 to 5 includes 1, 1.5, 2, 2.75, 3, 3.80, 4, 5, etc.).

A nucleotide (nt) consists of a phosphate group linked by a phosphoester bond to a pentose (ribose in RNA, and deoxyribose in DNA) that is linked in turn to an organic base. The monomeric units of a nucleic acid are nucleotides. Naturally occurring DNA and RNA each contain four different nucleotides: nucleotides having adenine, guanine, cytosine and thymine bases are found in naturally occurring DNA, and nucleotides having adenine, guanine, cytosine and uracil bases are found in naturally occurring RNA. The bases adenine, guanine, cytosine, thymine, and uracil often are abbreviated A, G, C, T and U, respectively.

Nucleotides include free mono-, di- and triphosphate forms (i.e., where the phosphate group has one, two or three phosphate moieties, respectively). Thus, nucleotides include ribonucleoside triphosphates (e.g., ATP, UTP, CTG and GTP) and deoxyribonucleoside triphosphates (e.g., dATP, dCTP, dITP, dGTP and dTTP), and derivatives thereof. Nucleotides also include dideoxyribonucleoside triphosphates (ddNTPs, including ddATP, ddCTP, ddGTP, ddITP and ddTP), and derivatives thereof.

Unless specified otherwise, nucleotides also include nucleotide analogs. Nucleotide analogs are synthetic nucleotides that can be used to replace natural nucleotides. Examples of nucleotide analogs include, for example, 5-dimethyluracil, 1-methyluracil, 2-amino-6-hydroxyaminopurine, 2-aminopurine, 3-methyluracil, 5-(hyroxymethyl)cytsosine, 5-bromouracil, 5-carboxycytosine, 5-fluoroorotic acid, 5-formylcytosine, 8-azadenine, 8-azaguanine, N6-hydroxyadinine, allopurinol, hypoxanthine, and thiouracil.

A polynucleotide, as used herein, may mean any molecule including a plurality of nucleotides, including but not limited to DNA or RNA. Preferably, the polynucleotide includes at least 5 nucleotides, and more preferably it includes 10 or more nucleotides. The depiction of a single strand also defines the sequence of the complementary strand. Thus, a nucleic acid also encompasses the complementary strand of a depicted single strand. A polynucleotide may be single stranded or double stranded, or may contain portions of both double stranded and single stranded sequence. Double stranded polynucleotides are a sequence and its complementary sequence that are associated with one another, as understood by those skilled in the art. The polynucleotide may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine, hypoxanthine, isocytosine and isoguanine. Polynucleotides may be obtained by chemical synthesis methods or by recombinant methods. When a polynucleotide has been defined as consisting of either DNA or RNA, it may be referred to as a DNA strand, or RNA strand, respectively.

An oligonucleotide, when used herein, refers to a polynucleotide as defined herein, except that oligonucleotides are generally smaller in length. An oligonucleotide includes a plurality of nucleotides, and therefore has a minimum size of 2 nucleotides, with a minimum of 6 nucleotides in some embodiments. With regard to their maximum size, oligonucleotides generally have a size of 100 nucleotides or less, with the limit being 70 nucleotides or less in some embodiments.

L-DNA is DNA containing L-deoxyribose rather than D-deoxyribose. It does not function as a template in DNA extension reactions because it is not recognized by generally used DNA polymerases. In addition, L-DNA forms a left-handed double helix (see FIG. 2), and thus is incapable of hybridizing to naturally-occurring D-nucleic acids and capable of hybridizing only to nucleic acids of the same L-form.

The term "primer", as used herein, refers to an oligonucleotide, occurring naturally as in a purified restriction digest or produced synthetically that is characterized by an ability to be extended against a template oligonucleotide, so that an oligonucleotide whose sequence is complementary to that of at least a portion of the template molecule is linked to the primer, when all are placed in the presence of nucleotides at a suitable temperature and pH. However, the mere ability to be used in this fashion does not require that primers be fully extended against a template, and in some embodiments, primers are used only as a site for the addition of a small number of non-templated nucleotides. The primers preferably have a length of at least 8 bases, more preferably at least 12 bases, and still more preferably at least 15 bases. The maximum chain length of the primers is not particularly limited, and is generally 50 bases or less, preferably 40 bases or less.

"Probe", as used herein, may mean an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence, depending upon the stringency of the hybridization conditions. There may be any number of base pair mismatches which will interfere with hybridization between the target sequence and the single-stranded nucleic acids described herein. However, if the number of mutations is so great that no hybridization can occur under even the least stringent of hybridization conditions, the sequence is not a complementary target sequence.

"Identical" or "identity" used herein in the context of two or more oligonucleotides, may mean that the sequences have a specified percentage of residues that are the same over a region of comparison. The percentage may be calculated by optimally aligning the two sequences, comparing the two sequences over the specified region, determining the number of positions at which the identical residue occurs in both sequences to yield the number of matched positions, dividing the number of matched positions by the total number of positions in the region of comparison, and multiplying the result by 100 to yield the percentage of sequence identity. "Substantially similar" means that a given nucleic acid sequence shares at least 85%, more preferably at least 90%, and even more preferably at least 95% identity with a reference sequence. In cases where the two sequences are of different lengths or the alignment produces one or more staggered ends and the specified region of comparison includes only a single sequence, the residues of single sequence may be included in the denominator but not the numerator of the calculation. When comparing DNA and RNA, thymine (T) and uracil (U) may be considered equivalent. Identity determination may be performed manually or by using a computer sequence algorithm such as BLAST or BLAST 2.0.

The term "antisense oligonucleotide", as used herein, refers to a single-stranded oligonucleotide with a base sequence complementary to a segment of another oligonucleotide that can specifically bind to the target oligonucleotide and inhibit its activity.

Complementary nucleotides are those which readily form base pairs in double stranded oligonucleotides. Adenine is complementary with thymine or uracil, and vice-versa, and guanine is complementary with cytosine, and vice-versa. Complementarity refers to the likelihood that opposing nucleotides in adjacent strands are complementary, with high complementarity indicating a high number of complementary nucleotides, and low-complementarity referring to a lower number of complementary nucleotides.

"Hybridization state," as used herein, refers to the degree to which two or more nucleotide sequences are bound to each other by traditional Watson-Crick complementary base-pairing or by other non-Watson-Crick binding modes including, but not limited to, trans-Watson-Crick pairings, Hoogsteen pairings, base-triplets, and quadruplexes.

The term "amplicon," as used herein, refers to an oligonucleotide that is the source and/or product of natural or artificial amplification or replication events. It can be formed using various methods including polymerase chain reactions.

"Hybridization probe," as used herein, refers to L-DNA structures that are optically detected and that respond to environmental conditions similarly to natural DNA that is identical in sequence and directly indicate the hybridization state. Other variants of the term "hybridization probe" include "annealing probe," which refers to L-DNA structures that indicate DNA hybridization and "melting probes" which refers to the L-DNA structures that indicate DNA denaturation, or dehybridization. Hybridization probes are not hinged structures. "Hinged structures" described in this application are used to indicate the hybridization state of the hinged probes and the temperature of their environment.

As used herein, the term "organic group" is used to mean a hydrocarbon group that is classified as an aliphatic group, cyclic group, or combination of aliphatic and cyclic groups (e.g., alkaryl and aralkyl groups). An alkaryl group is a an aryl group that is attached to the remainder of the structure by an intervening alkyl group, whereas an aralkyl group is an aryl group that is attached directly to the structure but that includes one or more additional alkyl groups attached thereto. In the context of the present invention, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Alkyl groups including 4 or fewer carbon atoms can also be referred to as lower alkyl groups. Alkyl groups can also be referred to by the number of carbon atoms that they include (i.e., $C_1$-$C_4$ alkyl groups are alkyl groups including 1-4 carbon atoms).

Cycloalkyl, as used herein, refers to an alkyl group (i.e., an alkyl, alkenyl, or alkynyl group) that forms a ring structure. Cyclic groups can be monocyclic or polycyclic and preferably have from 3 to 10 ring carbon atoms. A cycloalkyl group can be attached to the main structure via an alkyl group including 4 or less carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

The term "aryl" as used herein includes carbocyclic aromatic rings or ring systems. The aryl groups may include a single aromatic ring, a plurality of separate aromatic rings, or a fused aromatic ring system. Carbocyclic aromatic rings do not include heteroatoms. Examples of aryl groups include phenyl, naphthyl, biphenyl, fluorenyl and indenyl. Aryl groups may be substituted or unsubstituted.

As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least". When used in the context of a process, the term "comprising" means that the process includes at least the recited steps, but may include additional steps. When used in the context of a compound or composition, the term "comprising" means that the compound or composition includes at least the recited features or components, but may also include additional features or components.

Figure 2:
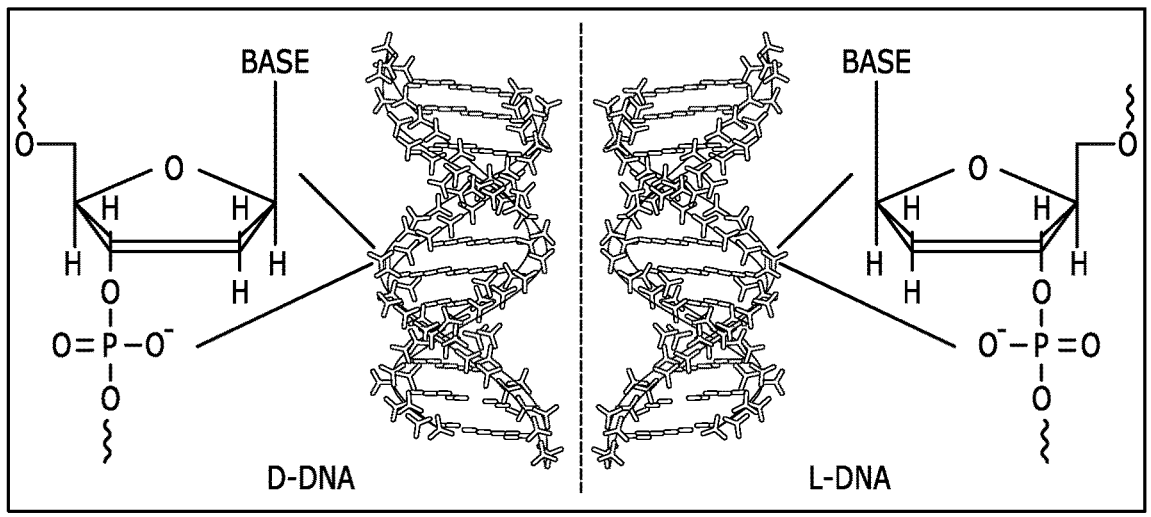
FIG. 2 provides an illustration showing that left-handed DNA, or L-DNA, is a synthetic enantiomer of naturally occurring, right-handed D-DNA.

The hybridization-triggered PCR (HT-PCR) design described herein overcomes the challenges of PCR failure and false negatives in PCR diagnostic applications by reducing the potential for false negatives and false positives in individually-prepared samples through the use of mirror-image DNA additives. Mirror-image DNA, or L-DNA, is a non-natural enantiomer of naturally occurring D-DNA (FIG. 2). L-DNAs share similar physical properties to D-DNAs, yet they are not compatible with each other (i.e., they do not base pair with each other). Likely for this reason, evolution chose to stick with just one form, the right-handed or D-DNA form. A number of groups have explored the utility of synthetic L-DNA in applications where DNA constructs are required but where biological interactions need to be minimized. For example, L-DNAs have been used to make non-cross-reactive molecular beacons (Kim, et al., Nucleic acids research 35, 7279-7287 (2007)), spiked controls for microarray quantification (Hauser et al., Nucleic acids research 34, 5101-5111 (2006)), biologically inert temperature probes for cells (Ke et al., J Am Chem Soc., 134, 18908-18911 (2012)), non-coding tags for PCR products (Hayashi et al., Nucleic Acids Symp Ser (Oxf), 261-262 (2005)), and nuclease insensitive aptamers (Williams et al., Bioactive and nuclease-resistant L-DNA ligand of vasopressin. Proc Natl Acad Sci USA., 94, 11285-11290 (1997)).

Figure 3A:
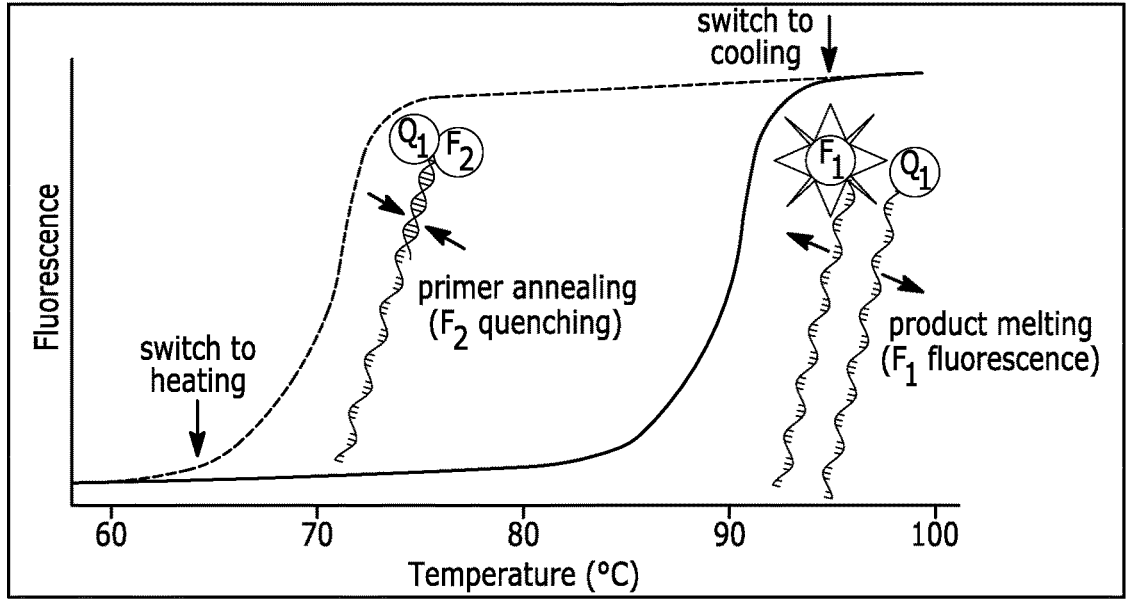
FIGS. 3A and 3B provide graphs showing the theoretical fluorescence profiles of L-DNA probes during thermal cycling for direct monitoring of annealing and melting of PCR reactants.

The inventors have developed a PCR approach based on the addition of L-DNA analogs of the D-DNA target product and primers to PCR. This provides two major advantages. First, because the L-DNAs share the same physical properties as the primers and PCR product, they enable dynamic monitoring of the primer annealing and amplicon melting by fluorescence (rather than estimates based on temperature) to identify the key moments to switch between heating and cooling (FIG. 3). This property is the reason for the "hybridization triggered PCR" or "HT-PCR" name. This enables a fundamentally simpler and more robust instrument design (FIG. 4) to retain PCR's high sensitivity in non-optimal settings and is the reason for "hybridization-triggered PCR" name. Secondly, because the L-DNA amplicon does not participate in the PCR amplification, it provides a means to incorporate within a single tube, a number of reaction controls. These include a critical control for verifying the extraction of target DNA from the patient sample. In addition it can serve as a constant diagnostic threshold indicator for single-tube PCR, and can be used as a template for verifying the final PCR product during melt analysis, retaining PCR's specificity in a single-tube setup.

Many advances have been made since Mullis' insight and testing of PCR. Mullis et al., Cold Spring Harbor symposia on quantitative biology 51 Pt 1, 263-273 (1986). A major breakthrough in PCR was the addition of fluorophores directly to the PCR reaction for real-time monitoring of PCR product, eliminating the need for gel electrophoresis product validation. This required the incorporation of optics in PCR instruments. The inventors have improved upon this by adding L-DNA analogs to the PCR reaction mixture and reusing the existing optics as a means to incorporate reaction controls necessary for interpreting single tube PCR diagnostic reactions, and as a means to monitor the hybridization state of the PCR reactants, eliminating the need for indirect temperature estimates and specification of the reaction timing.

Because this approach focuses on the hybridization state of the PCR reactants rather than temperature and timed steps, the instrumentation in combination with L-DNA reaction additives identifies the key moments for modulation between heating and cooling phases, resulting in self-calibrated cycling conditions based on the individual reaction contents. The optical indicator for the L-DNA amplicon "melt" state is used switch from heating to cooling, and the optical indicator for the L-DNA primer "anneal" state is used to switch from cooling to heating, independent of the temperature of the reaction (see FIG. 3). For example, this design is not affected by sample variation in salt concentrations. Using traditional PCR the salt affects the annealing state of the D-DNA participating in the PCR reaction, changing the temperature required to achieve annealing, which may lead to low PCR efficiency, poor specificity, or complete reaction failure. These effects are overcome by the present invention since the decision to switch to heating is determined by the hybridization state of the L-DNA counterparts, which are equally affected by the sample variations in salt concentration.

A second advantage was the impact of the L-DNA additives as reaction controls for single-tube PCR. For example, L-DNA probes can be used in methods for using the L-DNA surrogates to verify sample rehydration, DNA recovery from patient sample, thermal cycling progression, diagnostic threshold, and product verification. The reuse of these L-DNAs as in-tube sample controls enables single-tube PCR by eliminating the costs and complexities related to running a series of parallel control samples and standards. In addition, the L-DNA-based controls provide important process feedback that is not contained in controls traditionally performed during PCR, including DNA recovery yield prior to target amplification and post-reaction melt analysis comparison of the L-DNA amplicon standard and the PCR product.

One application of particular interest is monitoring the hybridization and dissociation of amplification product strands and primers during polymerase chain reaction (PCR). The thermal cycling that is required for PCR is generally controlled by monitoring temperature, which is an easy-to-measure but indirect indicator of the hybridization state of the nucleic acid structures (e.g., amplification products, or amplicons, melt at ~95° C., and primers anneal at 55°-70° C., as determined beforehand experimentally or by using predictive oligonucleotide hybridization software). Furthermore, the temperature of a PCR sample is generally determined using a thermal sensor located outside of the sample, so as to not contaminate the sample, which further propagates the delay and error in the measurement. Although algorithms and heating methods have been developed to be reasonably accurate, they generally cannot be universally applied across instruments, individual PCR assays, and do not account for unexpected reaction conditions (e.g., excess salts or divalent ions).

Figure 5:
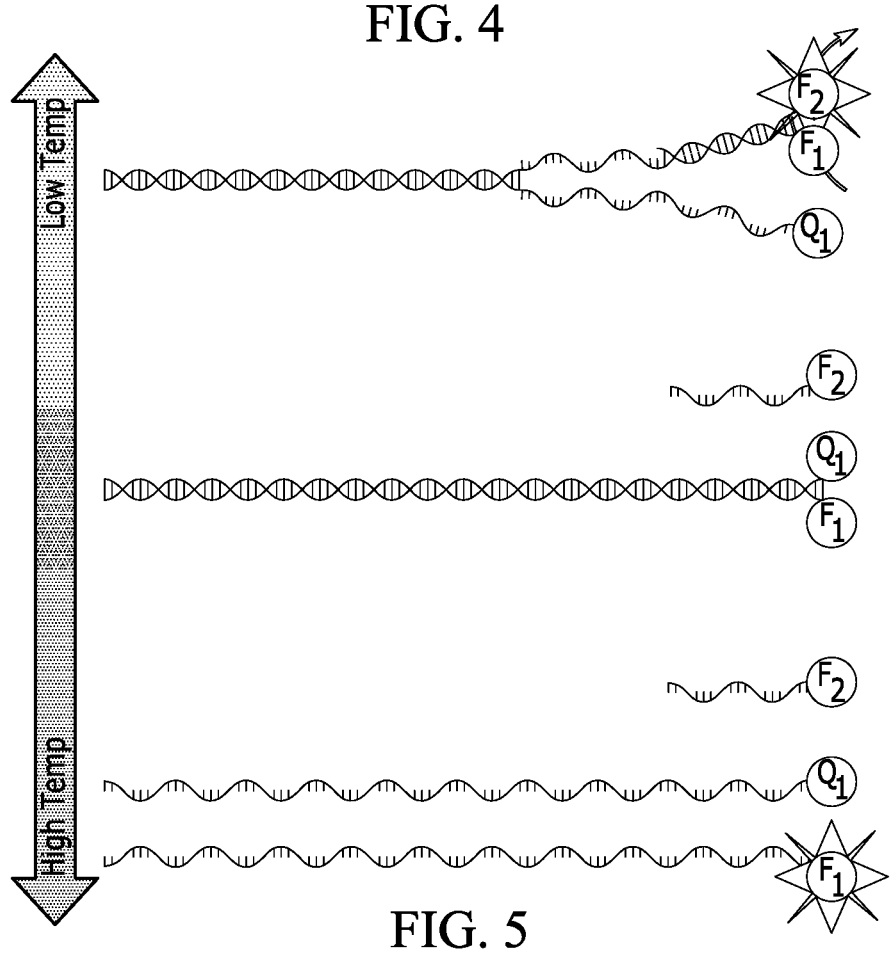
FIG. 5 provides a schematic representation showing the potential hybridization states and fluorescence responses of annealing and melting L-DNA probes at the low temperatures of PCR (50-70° C.) and at high temperatures of PCR 85-99° C.).
Figure 6:
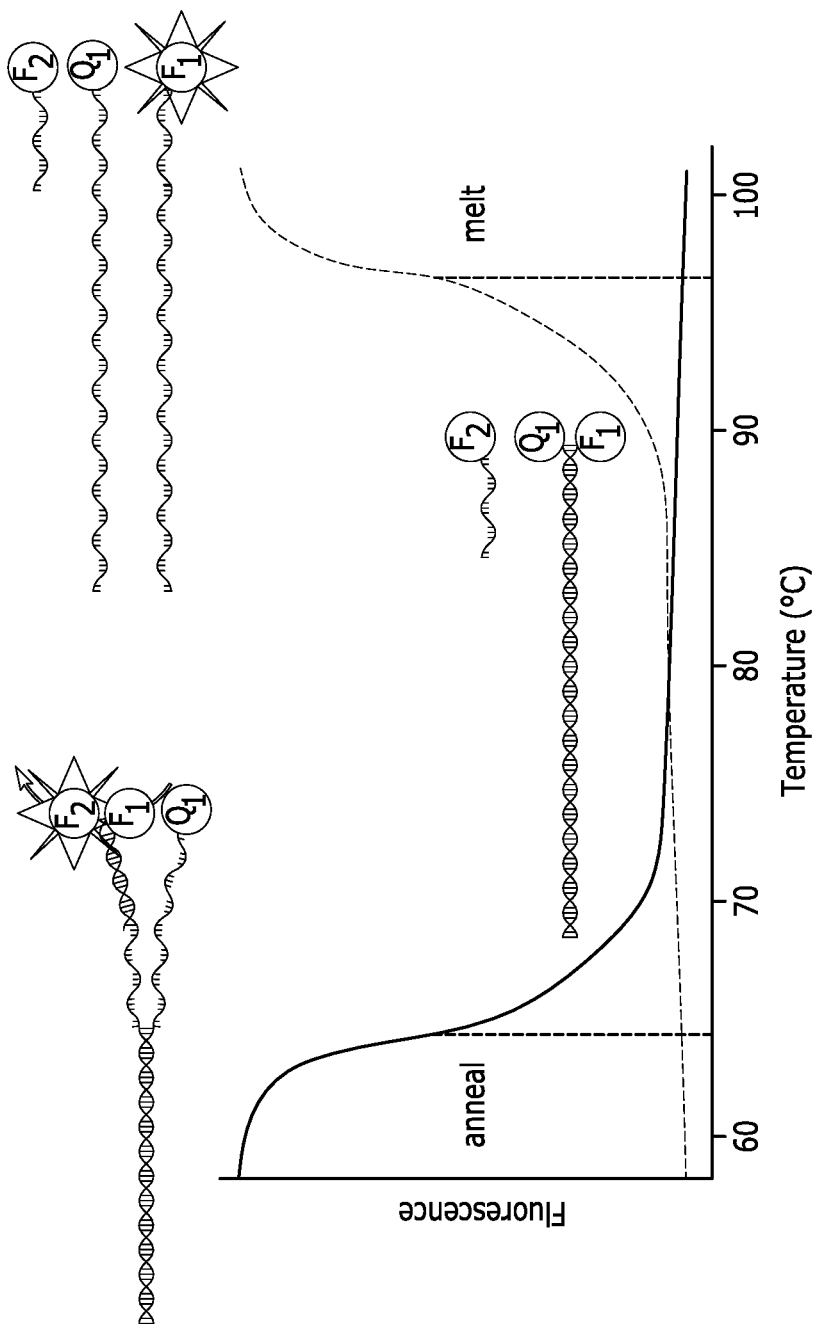
FIG. 6 provides a graph and schematic representation showing the association of the annealing and melting L-DNA probes over a range of temperatures and how they change their hybridization state and fluorescence emission during annealing and melting.

The L-DNA based systems and methods described in this application could be used to directly and accurately monitor the nucleic acids involved in PCR (amplification product strands and primers) to more precisely control the heating and cooling inputs of the instrument. Specifically, analogs to the PCR amplification products and primers, such as enantiomeric L-DNA structures, could be used to identify the PCR phase (i.e., primer annealing or amplicon melting phases) (FIGS. 5 and 6). The hybridization state of enantiomeric structures (i.e., unnatural L-DNA) identical to the amplification products and primers (i.e., naturally occurring D-DNA) that are present in the PCR reaction are used. Using identical enantiomers to those used in PCR (i.e., D-DNAs) would not work, because they would interfere with the reaction by binding to the sequences used in the amplification reaction and be amplified themselves by the polymerase. Part of what makes this work is that L-DNA sequences that are synthesized to be identical in sequence to their D-DNA counterparts have identical physical properties in the ways that are important to making PCR work, including their binding constants, melt temperatures, hybridization temperatures, and response to the presence of environment reaction conditions (i.e, buffer components, pH, salt, magnesium). Importantly, complementary D-DNA strands and polymerase enzymes do not bind to L-DNA oligonucleotides.

Melting and Annealing L-DNA Probes

In one aspect, the present invention provides L-DNA probes that can be used to monitor and analyze DNA hybridization state. The probes of the present invention include one or more polynucleotide sequences that include associated fluorescent dye compounds (covalently or non-covalently attached) for monitoring hybridization state. The L-DNA probes of the present invention monitor DNA hybridization state by mimicking the behavior of nucleotide sequences of interest, while not interacting with them as a result of their incompatible L-DNA structure. The L-DNA probes are polynucleotides that include one or more fluorescent dye compounds that respond to hybridization of the L-DNA probe with a complementary nucleotide sequence. In some embodiments, the L-DNA probes are linear sequences including a single fluorescent dye compound at one end of the polynucleotide, while in other embodiments, the L-DNA probes are polynucleotides capable of forming a hairpin structure that including a fluorescent dye compound at each end of the polynucleotide. The L-DNA probes can include a range of different sizes. In some embodiments, L-DNA probes (e.g., the annealing and melting probes) have a size of from 15 to 200 nucleotides.

The L-DNA probes are designed to produce positive fluorescence signal at the melting phase of PCR when the 'sense' and 'antisense' L-DNA PCR amplification product analog strands dissociate at high temperatures (quencher is separated from the fluorophore), and at the annealing phase of PCR when the primer and 'sense' L-DNA strand anneal at low temperatures (FRET generated when the fluorophores come together). Alternatively, both the melting and annealing phases could use quencher pairs, which would produce negative signal at the lower temperature annealing phase of PCR. When looking at the derivative of the fluorescence profiles at these annealing and melting phases, the local minimum or maximum derived values could be used interchangeably.

Figure 3B:
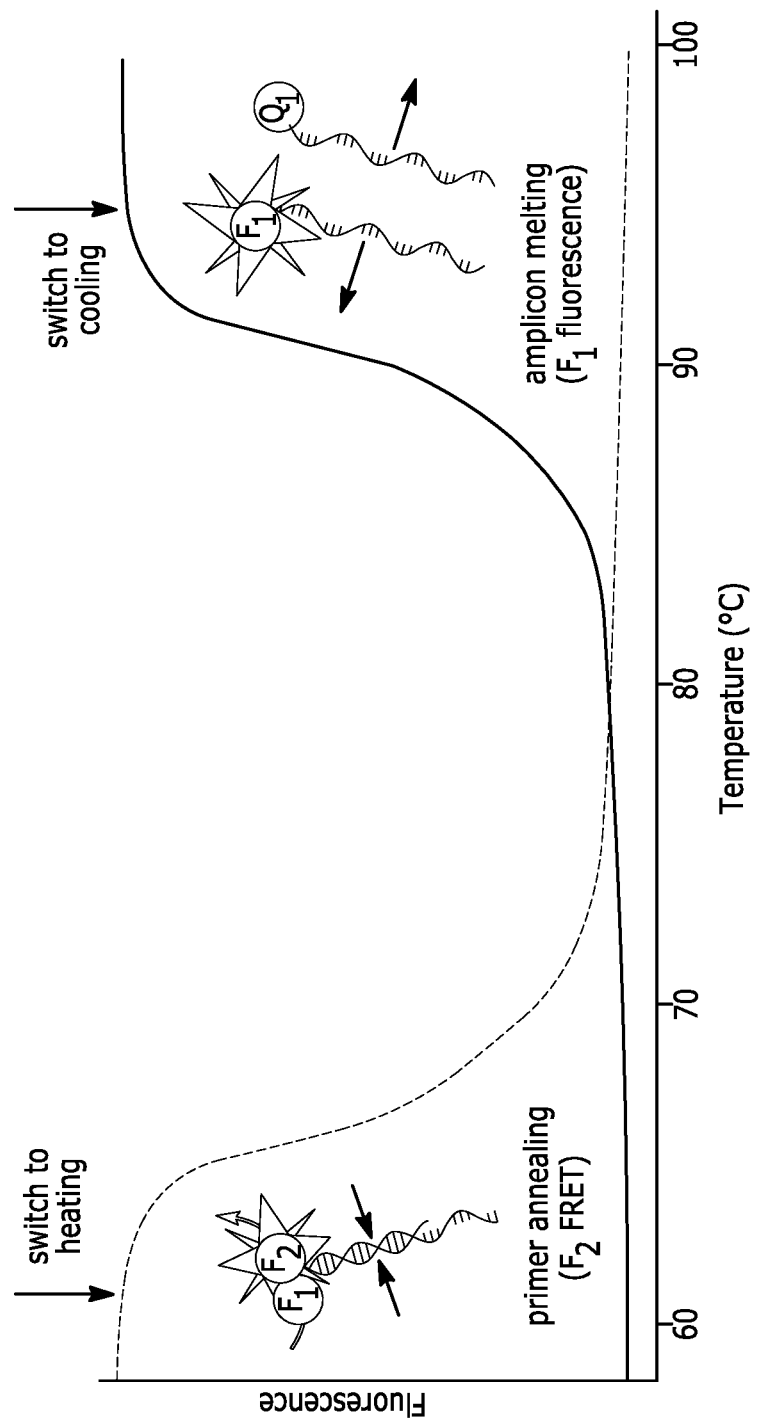
Figure 7:
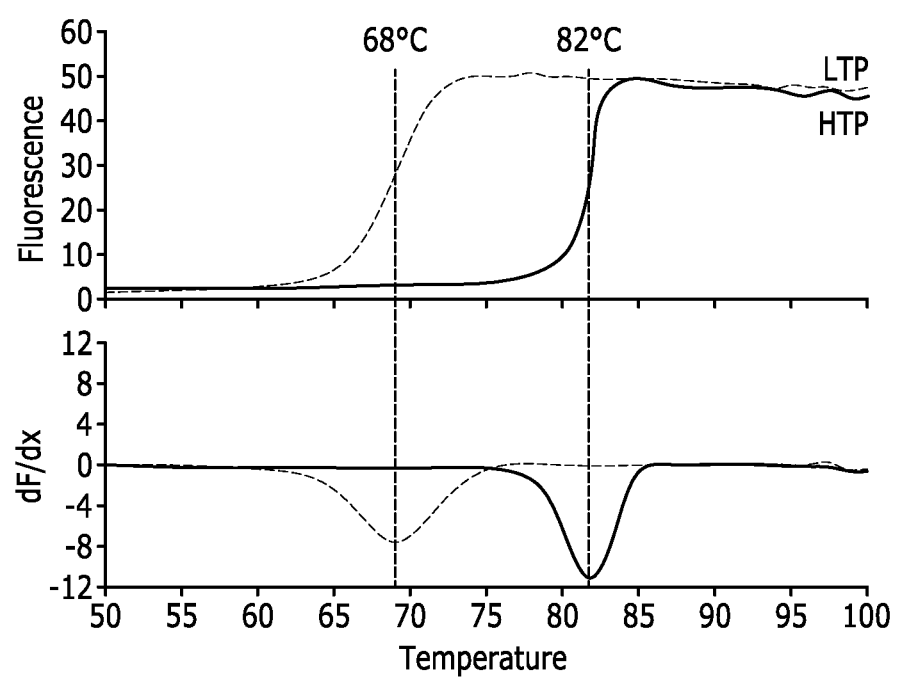
FIG. 7 provides a graph showing data that demonstrates that the annealing and melting L-DNA probes function as hybridization sensors. Upper panel shows the measured fluorescence for a melting L-DNA probe (HTP) and a annealing L-DNA probe (LTP) as a function of reaction temperature. The lower panel plots the derivatives of the curves shown in the upper panel.
Figure 8:
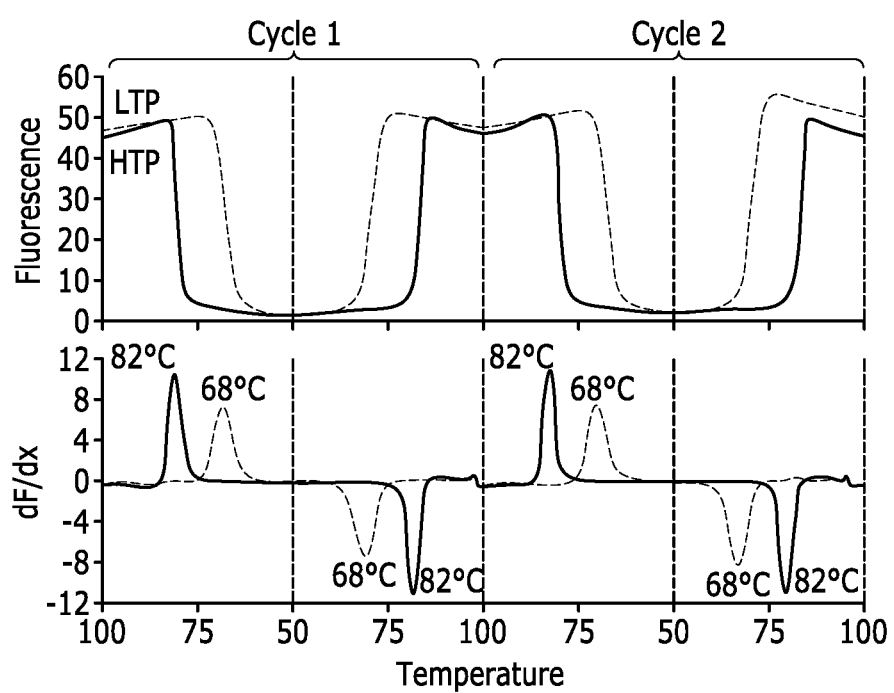
FIG. 8 provides graphs showing that the annealing and melting L-DNA probes function during rounds of thermocycling. Upper panel shows the measured fluorescence for a melting L-DNA probe (HTP) and a annealing L-DNA probe (LTP) as a function of reaction temperature. The lower panel plots the derivatives of the curves shown in the upper panel.

Use of the L-DNA probes is illustrated by an exemplary probe using a FRET pair as the fluorescent dye component. The "annealing" phase of PCR will be detected using L-DNA structures of the 'sense' strand of the DNA being amplified and the primer. An example of one embodiment of the L-DNA probes is shown in FIG. 3B and in FIG. 5. In this embodiment, the 'sense' strand has a fluorescent compound (F1, FRET donor) incorporated on the 3' end and the primer has a fluorescence FRET pair (F2, FRET acceptor) incorporated on the 5' end. As the temperature in the tube decreases the self-hybridizing stem region begins to form and fluorescence at the wavelength associated with the FRET fluorescent compound F2 is detected. The "melting" phase of PCR is detected using an L-DNA structure of the 'antisense' strand of the DNA being amplified. This 'antisense' strand has a fluorescence quencher compatible with the F1 fluorophore on the 3' end. As the temperature in the tube increases the 'sense' and 'antisense' strands dissociate and fluorescence at the wavelength associated with the fluorescent compound F1 is detected. Preliminary results using D-DNA structures indicated that this design can be used for optically sensing these molecular structures during thermal cycling (FIGS. 7 and 8). This could also work with fluorophores and a primer designed for the opposite end of the 'sense' and 'antisense' strands, or where the primer strand is the FRET donor and the 'sense' strand is the FRET acceptor.

The L-DNA probes can be linear or hairpin L-DNA probes. An example of linear L-DNA probes is shown in FIG. 5. In a system using linear L-DNA probes, the linear polynucleotides typically include a primer polynucleotide, a target polynucleotide, and a polynucleotide that is antisense (i.e., complementary) to the target polynucleotide sequence. At low temperature, the primer and the target sequence bind, resulting in the fluorescent dye compounds present in these polynucleotides become adjacent. As temperature increases, the primer and the target polynucleotide separate, and the target polynucleotide and the antisense polynucleotide hybridize, resulting in two fluorescent dye compounds again becoming adjacent. Finally, as the temperature increases further, all of the polynucleotide strands become separate, such that none of the fluorescent dye compounds remain adjacent.

Figure 9:
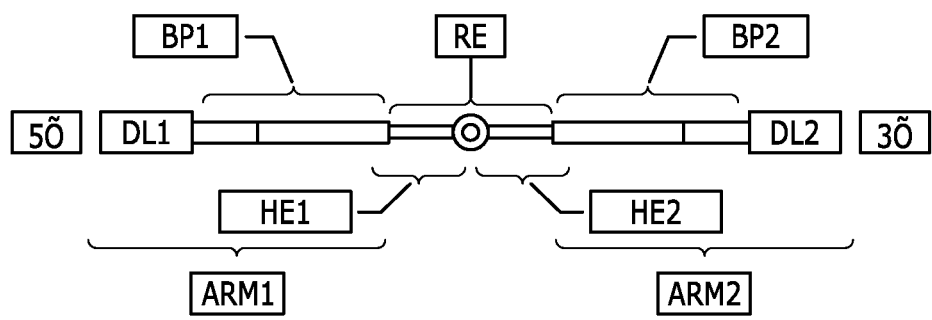
FIG. 9 provides a schematic representation of an L-DNA probe having a hairpin configuration.
Figure 10:
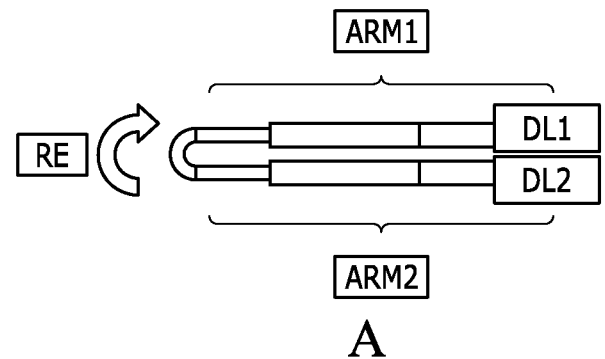
FIGS. 10A and 10B provide schematic representations of the L-DNA probe in (A) a folded state and (B) an elongated state.
Figure 10:
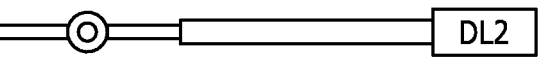

In some embodiments, the L-DNA probes are hairpin L-DNA probes. The terms "hairpin structure" refers to stable loop structures formed by pairing with another single-stranded region in the same molecule. FIG. 9 shows the general configuration of an L-DNA probe having a hairpin configuration, the various elements are described as: DL1 and DL2 represent matched pairs of detectable labels such as fluorophores and appropriate quenchers to suppress fluorescence or fluorescent partners capable of fluorescent energy transfer (FRET). BP1 and BP2 represent suitable binding or associating partners that non-covalently bind or associate with one another by such mechanisms as van der Walls, hydrophobic, aromatic, π-π interaction such as association between alkyl hydrocarbon chains, aromatic interactions and the like, as well as hydrogen bonding, for example such as by Watson-Crick base pairing for poly nucleotides. It is noted that for association of specific regions they must be of the same optical form such as L forms associate with complementary L forms but not L forms associating with a complementary D form of the polynucleotide elements. HE1 and HE2 represent hinge elements that allow ARM1 and ARM2 to associate with one another at temperatures below their melting or disassociation point. Hinge elements may be composed of polynucleotides of their D or L forms but should be single stranded and not capable of binding with polynucleotides in a sample. Alternately, the hinge elements can be composed of a non-nucleotide organic group. RE represents a point of rotation or flexibility about which HE1 and HE2 may rotate or flex or bend to allow the ARMs 1 and 2 to associate with one another below their melting temperatures and allow the ARMs 1 and 2 to disassociate at temperatures above their melting point. It is noted that the association of the arms may be subject to interactions other than temperature such as pH, presence of certain substances and other forms of association and disassociation. Such examples are alkyl-alkyl interactions of the arms are composed of alkyl chains, salt bridges if the BP elements of the ATMs are composed of a poly primary amine containing BP1 and a carboxylic acid containing BP2 which can form ionic pairs or salt bridges to associate with one another but separate from one another under changes in pH that differ from their pH of association. Such a probe is useful for example to determine the pH of interior regions of cells. The change from an associated form to an extended form of the L-DNA probe can be measured by the interaction or differences in signal obtained provided by the detectable labels DL1 and DL2. The detectable labels do not necessarily have to be at the respective ends of the structure, but may be located at various positions within their respective ARMs as long as their signals can be differentiated from one another in the folded state of the L-DNA probe and its unfolded or elongated state under the conditions suitable for achieving either association or disassociation of the two ARMs such as temperature changes or pH changes and the like. FIG. 10 provides a schematic representation of the L-DNA Probe in folded state (A) and an elongated state (B).

Oligonucleotides and polynucleotides of the invention can be synthesized by a number of approaches, e.g. Ozaki et al, Nucleic Acids Research, 20: 5205-5214 (1992); Agrawal et al, Nucleic Acids Research, 18: 5419-5423 (1990); or the like. The oligonucleotide probes of the invention are conveniently synthesized on an automated DNA synthesizer, e.g. a Perkin-Elmer (Foster City, Calif.) Model 392 or 394 DNA/RNA Synthesizer, using standard chemistries, such as phosphoramidite chemistry. Alternative chemistries, e.g. resulting in non-natural backbone groups, such as phosphorothioate, phosphoramidate, and the like, may also be employed provided that the hybridization efficiencies of the resulting oligonucleotides are not adversely affected.

Synthesis of L-DNA probes can be conducted using methods identical to those used for the preparation of D-DNA probes, except using L-DNA starting materials (e.g., L-DNA amidite) instead of D-DNA starting materials (e.g., D-DNA amidites). L-DNA amidite starting material is commercially available and can be purchased, for example, from ChemGenes Corporation in Wilmington, Mass. L-DNA oligonucleotides are also commercially available. For example, L-DNA oligonucleotides can be purchased from BioSynthesis, Inc. in Lewisville, Tex. and from Biomers.net in Ulm, Germany.

In one aspect, the present invention provides an L-DNA probe capable of forming a hairpin structure that includes a first polynucleotide arm having a fluorescent dye component at a first end and connecting to a hinge region at the second end, and a second polynucleotide arm having a fluorescent dye component at a first end and connecting to the hinge region at a second end, wherein the hinge region consists of a non-nucleotide organic group including from 6 to 60 carbon atoms, and the first and second polynucleotide arms are L-DNA.

In some embodiments, the L-DNA probe is an annealing probe wherein the first polynucleotide arm consists of a target polynucleotide region and the second polynucleotide arm consists of a primer nucleotide region. In other embodiments, the L-DNA probe is a melting probe wherein the first polynucleotide arm consists of a target polynucleotide region and the second polynucleotide arm consists of an antisense polynucleotide region.

In some embodiments, the hybridization state of the annealing and melting L-DNA probes is monitored and analyzed using fluorescent dyes and/or quenchers to produce FRET (Forster Resonance Energy Transfer) or fluorescence quenching. For FRET-based monitoring of hybridization state, an annealing L-DNA probe includes a first L-DNA polynucleotide comprising the target polynucleotide and including a fluorescent dye FRET-acceptor component at the 3' end of the first L-DNA polynucleotide and a second L-DNA polynucleotide comprising the primer polynucleotide and including a fluorescent dye FRET-donor at the complementary 5' end of the second L-DNA polynucleotide, and the melting L-DNA probe includes a third L-DNA polynucleotide having a sequence antisense to the target polynucleotide sequence and including a fluorescent dye FRET-donor at the complementary 5' end of the third L-DNA polynucleotide.

In an alternative FRET-based arrangement, the annealing L-DNA probe includes a first L-DNA polynucleotide comprising the target polynucleotide and including a fluorescent dye FRET-donor component at the 3' end of the first L-DNA polynucleotide and a second L-DNA polynucleotide comprising the primer polynucleotide and including a fluorescent dye FRET-acceptor at the complementary 5' end of the second L-DNA polynucleotide, and the melting L-DNA probe includes a third L-DNA polynucleotide having a sequence antisense to the target polynucleotide sequence and including a fluorescent dye FRET-acceptor at the complementary 5' end of the third L-DNA polynucleotide.

For a fluorescence quenching-based monitoring of hybridization state, an annealing L-DNA probe includes a first L-DNA polynucleotide comprising the target polynucleotide and including a fluorescence quenching dye component at the 3' end of the first L-DNA polynucleotide and a second L-DNA polynucleotide comprising the primer polynucleotide and including a fluorescent dye at the complementary 5' end of the second L-DNA polynucleotide, and the melting L-DNA probe includes a third L-DNA polynucleotide having a sequence antisense to the target polynucleotide sequence and including a fluorescent dye at the complementary 5' end of the third L-DNA polynucleotide.

In an alternative embodiment, fluorescence quenching-based arrangement an annealing L-DNA probe includes a first L-DNA polynucleotide comprising the target polynucleotide and including a fluorescent dye component at the 3' end of the first L-DNA polynucleotide and a second L-DNA polynucleotide comprising the primer polynucleotide and including a fluorescence quenching dye at the complementary 5' end of the second L-DNA polynucleotide, and the melting L-DNA probe includes a third L-DNA polynucleotide having a sequence antisense to the target polynucleotide sequence and including a fluorescence quenching dye at the complementary 5' end of the third L-DNA polynucleotide.

For monitoring hybridization state using a combination of FRET and fluorescence quenching, an annealing L-DNA probe includes a first L-DNA polynucleotide comprising the target polynucleotide and including a FRET-acceptor fluorescent dye component at the 3' end of the first L-DNA polynucleotide and a second L-DNA polynucleotide comprising the primer polynucleotide and including a FRET-donor fluorescent dye at the complementary 5' end of the second L-DNA polynucleotide, and the melting L-DNA probe includes a third L-DNA polynucleotide having a sequence antisense to the target polynucleotide sequence and including a fluorescence quenching dye at the complementary 5' end of the third L-DNA polynucleotide."

Hairpin L-DNA probes can include hinge regions that are made from an oligonucleotide strand, or from a non-nucleotide organic group. There are several non-oligonucleotide elements that can be employed to produce the hinge region of the L-DNA probes described herein. In some embodiments, the non-nucleotide organic group of the hinge region is an aliphatic alkyl group. In other embodiments, the non-nucleotide organic group of the hinge region is a polyethylene glycol chain. The hinge region can vary in size. In some embodiments, the hinge region can include from 6 to 100 carbon atoms, while in other embodiments, the hinge region can include from 6 to 80 carbon atoms, from 6 to 60 carbon atoms, or from 6 to 40 carbon atoms.

In some embodiments, phosphoramidites are used to synthesize the hinge region. Various alkyl groups are available as phosphoramidites thus are amenable to straight forward incorporation during routine synthesis of polynucleotides employing phosphoramidite chemistry. Among these are c3 linkers comprised of a single polypropylene unit as a phosphoramidite and can be employed to join the two complementary oligonucleotides at their 5' and 3' ends to provide a flexible hinge. Additional suitable hinge elements available as phosphoramidites are comprised of 6, 9 or 18 repeats of ethylene glycol units which likewise can be employed to provide a hinge between the two complementary elements of the thermo-sensing oligonucleotide elements of the thermo-sensing probes. Interestingly and surprisingly, the non-nucleotide elements increased the melting temperature of the thermo-sensing probes by significant amounts that is by from 3° C. to about 20° C. That is to say that a hinge element consisting of a single hexaethylene glycol unit increased the Tm of the thermo-sensing probe by more than 10° C. which would have required an additional 6 to 10 additional complementary nucleotides to produce a similar effect. Similarly, a hinge element can be synthesized via phohoramidite chemistry by constructing the hinge from contiguous 1',2' dideoxyribose units to afford a hinge comprised of the desired number of repeats of the 1',2' dideoxyribose units. Hinge elements can be prepared consisting of combinations of the various hinge elements to afford hinge regions with other desirable properties to afford purification, modify Tm and the like. Non-nucleotide hinge elements eliminate the off target or promiscuous hybridization of hinge elements comprised of nucleotides as the non-nucleotide elements cannot participate in nucleotide hybridization reactions.

Desirable hinge elements may not be available as phosphoramidites for synthesis and hinge elements can be added to the oligonucleotides to provide a non-nucleotide hinge element using alternative chemistries. For example the 5' end of one of the complementary oligonucleotide thermo-sensing elements can have a terminal thiol or thio phosphate and the second complementary thermo-sensing oligonucleotide element can also have a thiol or thiophosphate at its 3' terminus and the hinge element can have a maleimide functionality at each of its termini. The di-maleimide hinge element is first reacted with one of the thermo-sensing oligonucleotide elements and purified to remove un-reacted oligonucleotides and un-reacted maleimide hinge elements thus providing a thermo-sensing oligonucleotide element joined to the hinge element via a thio ester linkage an having its un-reacted maleimide termini available for reaction. This purified maleimide-activated hinge-thermo-sensing oligonucleotide is then reacted with the complementary thiol modified thermo-sensing probe oligonucleotide and purified to remove un-reacted reaction material to provide a complete thermo-sensing probe consisting of the two complementary thermo-sensing oligonucleotides joined to one another by the hinge element at their respective 3' and 5' ends. Other means of conjugating the non-nucleotide hinges to the thermo-sensing oligonucleotide segments such as amide formation by reaction between primary amines and activated carboxylic acids or "click chemistry" are well known in the art and are suitable for introduction of non-nucleotide hinge elements into the thermo-sensing probes described in this application. The below table provides some suitable hinge elements and end joining chemistries to afford introduction or incorporation of the hinge elements into thermo-sensing probe or as hinges in other oligonucleotides.

It is further noted that should the various elements of the probes be comprised of nucleic acids xeno-polynucleotides such as morpholino, peptide, bridged, locked and other backbone configurations or those of mixed compositions are also suitable for making and using the described sensing probes. Additionally modified or other non-natural nucleotides may also be used in the construction of such L-DNA probes. Such L-DNA probes are of particular utility in monitoring the temperature or other conditions in certain biological in vitro reactions such as polymerase chain reaction, isothermal nucleic acid amplification reactions and intracellular temperature or sensing of other conditions such as pH in microenvironments where the non-hinge regions of the L-DNA probe may unfold or fold to provide detectable signals correlated with such environmental states or substance affording these changes in the state of the probe.

Importantly the L-DNA probes can be used within reactions either static or batch type reactions or conditions or in streams under flow reaction conditions or operating conditions may need to be monitored. Further, the L-DNA probes can be encapsulated in optically transparent plastic, glass or other containers/vessels or capsules to isolate the sensors from the reaction of process materials yet provide feedback on the temperature conditions of the material in which the encapsulated L-DNA probes are placed or located. The sensor response provides real-time feedback via suitable interrogation such as electro-optical devices to make adjustments to operating temperature in particular processes such as biological reactions or other processes where such monitoring and feed-back are necessary or desirable to maintain and monitor such conditions. In addition the sensing probes described can be affixed to a solid surface such as a reaction tube, a tube wall, nano or micro particles, to magnetic beads, to the tips of fiber optics.

Fluorescent Dye Components

The hybridization state of L-DNAs can be monitored and analyzed using a variety of different types of covalently attached dyes, including fluorescent dye/quencher pairs. FRET pairs, intercalating dyes, and minor groove-binding dyes. Depending on the nature of the dye, fluorescence occurs either if the L-DNA to which it is attached is in a double stranded, or single stranded form. For example, FRET pairs only fluoresce in the double stranded form, whereas fluorescent dye/quencher pairs only fluoresce in the single stranded form.

In some embodiments, the probes include fluorescent and quencher molecules attached to the oligonucleotide. In this embodiment, the first fluorescent dye component is a fluorescent compound and the second fluorescent dye component is a quencher. As used herein, the terms "quenching" or "fluorescence energy transfer" refer to the process whereby when a fluorescent molecule and a quencher molecule are in close proximity, whenever the fluorescent molecule is excited, a substantial portion of the energy of the excited state nonradiatively transfers to the quencher where it either dissipates nonradiatively or is emitted at a different emission wavelength than that of the fluorescent molecule.

It is well known that the efficiency of quenching is a strong function of the proximity of the fluorescent molecule and the quencher, i.e., as the two molecules get closer, the quenching efficiency increases. As quenching is strongly dependent on the physical proximity of the reporter molecule and quencher molecule, it has been assumed that the quencher and reporter molecules must be attached to the probe within a few nucleotides of one another, usually with a separation of about 6-16 nucleotides. Ozaki et al, Nucleic Acids Research, 20: 5205-5214 (1992). Typically, this separation is achieved by attaching one member of a reporter-quencher pair to the 5' end of the probe and the other member to a base 6-16 nucleotides away.

By placing the fluorescent and quencher molecules at seemingly remote locations on the oligonucleotide, differential quenching can be seen between the single stranded state and the double stranded state, i.e., hybridized state, of the oligonucleotide probe, e.g., Bagwell et al., Nucleic Acids Research, 22(12): 2424-2425 (1994). Preferably, fluorescent molecules are fluorescent organic dyes derivatized for attachment to the terminal 3' carbon or terminal 5' carbon of the probe via a linking moiety. Preferably, quencher molecules are also organic dyes, which may or may not be fluorescent, depending on the embodiment of the invention. For example, in a preferred embodiment of the invention, the quencher molecule is fluorescent. Generally, whether the quencher molecule is fluorescent or simply releases the transferred energy from the fluorescent molecule by non-radiative decay, the absorption band of the quencher should substantially overlap the fluorescent emission band of the fluorescent molecule. Non-fluorescent quencher molecules that absorb energy from excited fluorescent molecules, but which do not release the energy radiatively, are referred to herein as chromogenic molecules.

Exemplary fluorescent-quencher pairs may be selected from xanthene dyes, including fluoresceins, and rhodamine dyes. Many suitable forms of these compounds are widely available commercially with substituents on their phenyl moieties which can be used as the site for bonding or as the bonding functionality for attachment to an oligonucleotide. Another group of fluorescent compounds are the naphthylamines, having an amino group in the alpha or beta position. Included among such naphthylamino compounds are 1-dimethylaminonaphthyl-5-sulfonate, 1-anilino-8-naphthalene sulfonate and 2-p-touidinyl-6-naphthalene sulfonate. Other dyes include 3-phenyl-7-isocyanatocoumarin, acridines, such as 9-isothiocyanatoacridine and acridine orange; N-(p-(2-benzoxazolyl)phenyl)maleimide; benzoxadiazoles, stilbenes, pyrenes, and the like.

In some embodiments, the fluorescent and quencher molecules are selected from fluorescein and rhodamine dyes. These dyes and appropriate linking methodologies for attachment to oligonucleotides are described in many references; e.g., Marshall, Histochemical J., 7: 299-303 (1975); Mechnen et al, U.S. Pat. No. 5,188,934; and Bergot et al. International application PCT/US90/05565.

In other embodiments, the fluorescent dye compounds used are Forster Resonance Energy Transfer (FRET) compounds. For example, the first and second fluorescent dye components can be a fluorescent energy transfer (FRET) pair. This mechanism involves a donor and acceptor pair wherein the donor molecule is excited at a particular wavelength, and subsequently transfers its energy non-radiatively to the acceptor molecule. This typically results in a signal change that is indicative of the proximity of the donor and acceptor molecules to one another.

Early methods of FRET based nucleic acid detection that lay a foundation for this technology in general, include work by Heller et al. (U.S. Pat. Nos. 4,996,143; 5,532,129; and U.S. Pat. No. 5,565,322, which are incorporated by reference). These patents introduce FRET based nucleic acid detection by including two labeled probes that hybridize to the target sequence in close proximity to each other. This hybridization event causes a transfer of energy to produce a measurable change in spectral response, which indirectly signals the presence of the target.

Cardullo et al. established that fluorescence modulation and nonradiative fluorescence resonance energy transfer can detect nucleic acid hybridization in solution. Cardullo et al., Proc. Natl. Acad. Sci. USA, 85:8790-8804, 1988. This study used three FRET based nucleic acid detection strategies. The first includes two 5' labeled probes that were complementary to one another, allowing transfer to occur between a donor and acceptor fluorophore over the length of the hybridized complex. In the second method, fluorescent molecules were covalently attached to two nucleic acids, one at the 3' end and the other at the 5' end. The fluorophore-labeled nucleic acids hybridized to distinct but closely spaced sequences of a longer, unlabeled nucleic acid. Finally, an intercalating dye was used as a donor for an acceptor fluorophore that was covalently attached at the 5' end of the probe.

There are many linking moieties and methodologies for attaching fluorescent dye compounds to the 5' or 3' ends of oligonucleotides, as exemplified by the following references: Eckstein, editor, Oligonucleotides and Analogues: A Practical Approach (IRL Press, Oxford, 1991); Zuckerman et al, Nucleic Acids Research, 15: 5305-5321 (1987)(3' thiol group on oligonucleotide); Sharma et al, Nucleic Acids Research, 19: 3019 (1991)(3' sulfhydryl): Giusti et al, PCR Methods and Applications, 2: 223-227 (1993) and Fung et al, U.S. Pat. No. 4,757,141 (5' phosphoamino group via Aminolink™ II available from Applied Biosystems, Foster City, Calif.); Stabinsky, U.S. Pat. No. 4,739,044 (3' aminoalkylphosphoryl group): Agrawal et al. Tetrahedron Letters, 31: 1543-1546 (1990)(attachment via phosphoramidate linkages); Sproat et al, Nucleic Acids Research, 15: 4837 (1987)(5' mercapto group); Nelson et al, Nucleic Acids Research, 17: 7187-7194 (1989)(3' amino group); and the like.

In other embodiments, binding dyes such as DNA-intercalating dyes are used. An early example of a DNA binding dye is Ethidium bromide. Ethidium bromide, like all other DNA binding agents used in kinetic PCR, is able to increase in fluorescent intensity upon binding. The resulting increase in signal can be recorded over the course of the reaction, and plotted versus the cycle number.

Binding dyes are relatively inexpensive as compared to other detection chemistries. The advantages of using these binding dyes are their low cost and excellent signal to noise ratios. Disadvantages include their non-specific binding properties to any double-stranded DNA in the PCR reaction, including amplicons created by primer-dimer formations. Wittwer et al., Biotechniques, 22:130-138, 1997.

SYBR™ Green I from Invitrogen™ (Carlsbad, Calif.) is a popular intercalating dye. Bengtsson et al., Nucleic Acids Res., 31:e45, 2003. SYBR™ Green I is a cyclically substituted asymmetric cyanine dye. A minor groove binding asymmetric cyanine dye known as BEBO, has been used in real-time PCR. BEBO causes a non-specific increase in fluorescence with time, perhaps due to a slow aggregation process and is less sensitive compared to SYBR™ Green I. A similar dye called BOXTO has also been reported for use in qPCR (Bengtsson et al., 2003). Like BEBO, BOXTO is less sensitive than SYBR™ Green I.

Other common DNA intercalating dyes include YO-PRO-1 and thiazole orange (TO) which are intercalating asymmetric cyanine dyes. Nygren et al., Biopolymers, 46:39-51, 1998 While these dyes exhibit large increases in fluorescence intensity upon binding, TO and Oxazole Yellow (YO) have been reported to perform poorly in real-time PCR (Bengtsson et al., 2003). Other dyes that may be used include, but are not limited to, pico green, acridinium orange, and chromomycin A3. Dyes that may be compatible with real-time PCR can be obtained from various vendors such as, Invitrogen, Cambrex Bio Science (Walkersville, Md.), Rockland Inc. (Rockland, Me.), Aldrich Chemical Co. (Milwaukee, Wis.), Biotium (Hayward, Calif.), TATAA Biocenter AB. (Goteborg, Sweden) and Idaho Technology (Salt Lake City, Utah) (U.S. Pat. No. 7,456,281). Additional DNA intercalating dyes include EvaGreen™ (Biotium) and LCGreen™ dye family (Idaho Technology).

PCR System Using Melting and Annealing L-DNA Probes

In one aspect, the invention provides a system for performing a polymerase chain reaction (PCR) and monitoring the reaction during temperature cycling using L-DNA, comprising: a sample container for holding a PCR sample including a target polynucleotide, a primer polynucleotide, and melting and annealing L-DNA probes including fluorescent dyes, a heat exchange component for heating or cooling the PCR sample, a control device for repeatedly operating the heat exchange component to subject the PCR sample to thermal cycling, an excitation source for optically exciting the PCR sample to detect the fluorescence of the melting and annealing L-DNA probes, a photodetector configured for detecting fluorescent emission from the melting and annealing L-DNA probes producing fluorescence data signals, and a processor configured to receive fluorescence data signals from the photodetector and process the signals to control the heat exchanger using the control device.

The polymerase chain reaction (PCR) is a technique widely used in molecular biology to amplify a piece of DNA by in vitro enzymatic replication. Typically, PCR applications employ a heat-stable DNA polymerase, such as Taq polymerase. This DNA polymerase enzymatically assembles a new DNA strand from nucleotides (dNTPs) using single-stranded DNA as template and DNA primers to initiate DNA synthesis. A basic PCR reaction requires several components and reagents including: a DNA template that contains the target sequence to be amplified; one or more primers, which are complementary to the DNA regions at the 5' and 3' ends of the target sequence; a DNA polymerase (e.g., Taq polymerase) that preferably has a temperature optimum at around 70.degree. C.; deoxynucleotide triphosphates (dNTPs); a buffer solution providing a suitable chemical environment for optimum activity and stability of the DNA polymerase; divalent cations, typically magnesium ions ($Mg^{2+}$); and monovalent cation potassium ions.

The majority of PCR methods use thermal cycling to subject the PCR sample to a defined series of temperature steps. Each cycle typically has 2 or 3 discrete temperature steps. The cycling is often preceded by a single temperature step ("initiation") at a high temperature (>90° C.), and followed by one or two temperature steps at the end for final product extension ("final extension") or brief storage ("final hold"). The temperatures used and the length of time they are applied in each cycle depend on a variety of parameters. These include the enzyme used for DNA synthesis, the concentration of divalent ions and dNTPs in the reaction, and the melting temperature (Tm) of the primers. Commonly used temperatures for the various steps in PCR methods are: initialization step—94-96° C.; denaturation step—94-98° C.; annealing step—50-65° C.; extension/elongation step—70-74° C.; final elongation—70-74° C.; final hold—4-10° C.

Real-time polymerase chain reaction, also called quantitative real time polymerase chain reaction (QRT-PCR) or kinetic polymerase chain reaction, is used to amplify and simultaneously quantify a targeted DNA molecule. It enables both detection and quantification (as absolute number of copies or relative amount when normalized to DNA input or additional normalizing genes) of a specific sequence in a DNA sample. Real-time PCR may be combined with reverse transcription polymerase chain reaction to quantify low abundance RNAs. Relative concentrations of DNA present during the exponential phase of real-time PCR are determined by plotting fluorescence against cycle number on a logarithmic scale. Amounts of DNA may then be determined by comparing the results to a standard curve produced by real-time PCR of serial dilutions of a known amount of DNA.

Multiplex-PCR and multiplex real-time PCR use of multiple, unique primer sets within a single PCR reaction to produce amplicons of different DNA sequences. By targeting multiple genes at once, additional information may be gained from a single test run that otherwise would require several times the reagents and more time to perform. Annealing temperatures for each of the primer sets should be optimized to work within a single reaction.

Figure 4:
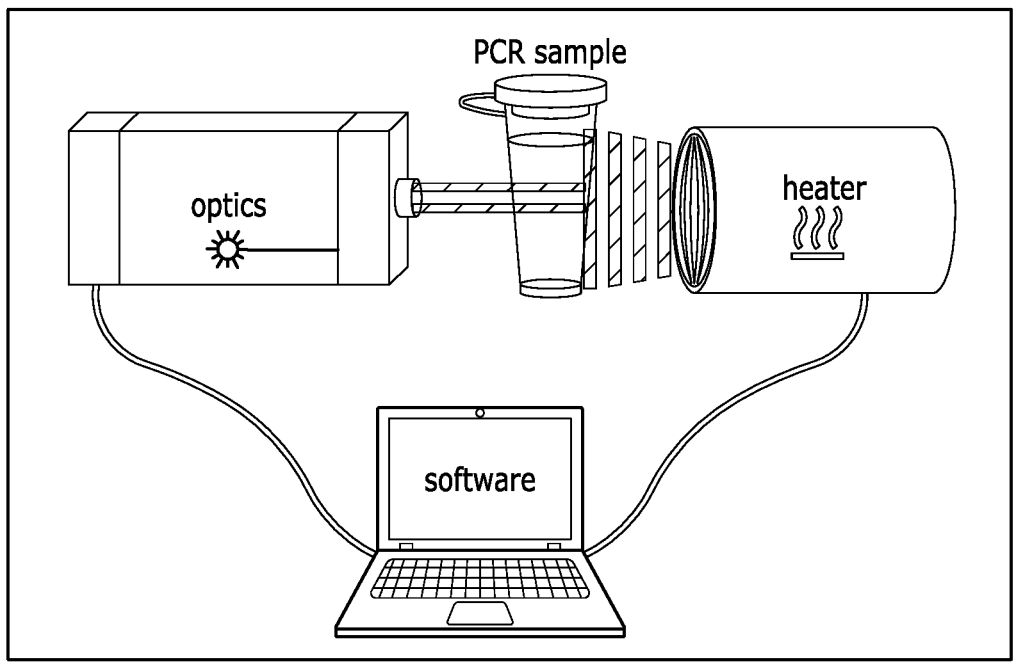
FIG. 4 provides a schematic representation showing that the HT-PCR instrument includes three components: 1) optics for monitoring hybridization of the L-DNA surrogates and PCR product, 2) software to switch between heating and cooling based on the L-DNA fluorescence-time profiles, and 3) a forced-air heater.

A scheme representing a real-time PCR thermal cycler device is provided in FIG. 4. The device would include optical sensors for monitoring structural state of the surrogate L-DNA molecules, rather than the thermometer inputs used for traditional PCR thermal cycling, and use these optical inputs for controlling the heating and cooling inputs for PCR thermal cycling. The sample is heated until the L-DNA analog of the PCR product produces fluorescence, indicating that the reaction can be cooled to promote the annealing of the primers. As the sample is cooled, the L-DNA analog of the primer anneals to the 'sense' strand and produce a change in fluorescence, indicating that the reaction can be heated to melt the PCR product strands. This process repeats for the duration of the reaction. The algorithm controlling the thermal cycling program could be developed to interpret the fluorescence using threshold fluorescence values or, more likely, the derivative of those values.

The L-DNA probes can be used for monitoring the PCR phase (primer annealing and PCR amplification product melting phases) as well as the generation of PCR product. This can be accomplished using fluorophores with separate wavelengths on the L-DNA structures and the PCR product, or by using the same wavelength of fluorophore for the L-DNA structures and the PCR product. In the case of the latter, the same fluorophores could be used by algorithms to de-convolute the signal of the two structures or by detecting the L-DNA structures during the first 5-10 cycles at a high optical gain (sensitivity) setting, then locking in cycling conditions to apply to the rest of the run while lowering the optical gain (sensitivity) setting to detect the PCR product (this method requires the L-DNA structures to be designed fluorescence at a much lower intensity than the PCR product fluorescence).

The method of monitoring a PCR method can use any of the L-DNA probes described herein. In some embodiments, the annealing L-DNA probe includes a first L-DNA polynucleotide comprising the target polynucleotide and including a first fluorescent dye component at the end of the first L-DNA polynucleotide and a second L-DNA polynucleotide comprising the primer polynucleotide and including a second fluorescent dye component at the complementary end of the second L-DNA polynucleotide, and the melting L-DNA probe includes a third L-DNA polynucleotide having a sequence antisense to the target polynucleotide sequence and including a third fluorescent dye component at the complementary end of the third L-DNA polynucleotide.

In another embodiment, the annealing L-DNA probe comprises a first polynucleotide consisting of a target polynucleotide region having a first dye component at its 3' end and a primer nucleotide region having a second dye component at its 5' end, with a hinge region between the target polynucleotide region and the primer nucleotide region, capable of forming a hairpin structure, and the melting L-DNA probe comprises a first polynucleotide consisting of a target polynucleotide sequence region having a first dye component at its 3' end and an antisense polynucleotide region having a third fluorescent dye component at its 5' end, with a hinge region between the target polynucleotide region and the antisense polynucleotide region, capable of forming a hairpin structure. In embodiments using L-DNA probes having a hairpin structure, the hinge region can include either an oligonucleotide, or non-nucleotide organic group. For example, in some embodiments, the hinge region of the melting and annealing L-DNA probes consists of an alkyl hydrocarbon or polyethylene glycol chain.

In other embodiments, the annealing L-DNA probe comprises a first polynucleotide consisting of a DNA intercalating dye, a target polynucleotide region and a primer nucleotide region, with a hinge region between the target polynucleotide region and the primer nucleotide region, capable of forming a hairpin structure, and the melting L-DNA probe comprises a DNA intercalating dye, a first polynucleotide consisting of a target polynucleotide sequence region and an antisense polynucleotide region, with a hinge region between the target polynucleotide region and the antisense polynucleotide region, capable of forming a hairpin structure.

PCR System Using Melting and Annealing L-DNA Probes

In another aspect, the invention provides a method of controlling temperature cycling of a polymerase chain reaction (PCR) comprising the steps of: (a) providing a PCR sample including a target polynucleotide and a primer, (b) adding melting and annealing L-DNA probes including fluorescent dyes to the PCR sample, (c) optically exciting the sample to allow the melting and annealing L-DNA probes to fluoresce, (d) heating the PCR sample to release the target polynucleotide by melting, and ending heating upon detection of fluorescence of the melting L-DNA probe, (e) cooling the PCR sample until the target polynucleotide and the primer have annealed, and ending cooling upon detection of fluorescence of the annealing L-DNA probe, and (f) heating the PCR sample to an extension temperature and providing a DNA polymerase and free nucleotides, thereby forming a new DNA strand complementary to the target polynucleotide.

The thermal cycling carried out in DNA amplification method such as PCR typically is carried out more than one. Accordingly, in some embodiments, steps (d) through (f) described above are repeated a plurality of times to amplify the target polynucleotide. For example, steps (d) through (f) can be repeated at least 5 times, at least 10 times, at least 15 times, at least 20 times, at least 25 times, at least 30 times, at least 35 times, at least 40 times, at least 45 times, or at least 50 times to amplify the target polynucleotide.

One advantage of the present invention is that use of L-DNA probes allows the thermal cycling to be carried out more rapidly. Accordingly, in some embodiments, the method allows steps (d) through (f) to be conducted in 20 seconds or less, 30 seconds or less, 40 seconds or less, or 50 seconds or less.

Many reactions are temperature sensitive. Of particular interest in diagnostics is the polymerase chain reaction (PCR) which is the methodology of choice for detecting small numbers of a nucleotide sequence in a solution. This reaction requires that the temperature of the reaction mixture vary between two or more reaction temperatures to achieve rapid geometric amplification of the number of copies of the target sequence in solution. Many of the reaction components and structures are very sensitive to the temperature of the solution and variations of a few degrees can completely inhibit the formation of additional copies. Therefore the control of the multiple temperature steps is critical to the success of these reactions. Because a sensor cannot be placed into the reaction tube itself, current PCR instruments estimate the temperature of the reaction by indirect means, usually by sensing the external temperature of the reaction tube or vessel and through prior instrument calibration estimating the temperature of the reaction vessel.

A more direct method would decrease the complexity of the PCR instrument design and provide better temperature control of these reactions. The design shown in FIG. 11 measures the temperature of the solution directly through an optical signal within the solution itself using thermally induced changes in nucleic acid structures. The L-DNA probes shown in this particular example are based on self-hybridizing molecular beacon type oligonucleotides. In this example two structures are added to the mix to sense both the high temperature and low temperature of a two temperature PCR reaction, typically 65° C. and 95° C. The design is based on optically sensing the closing and opening of DNA self-hybridizing structures. The low temperature (i.e., annealing) probe (labeled LTP) works by incorporating a fluorescent compound (F1) and a fluorescence FRET pair (F2) on each of the ends of the self-hybridizing stem region (ends). As the temperature in the tube decreases the self-hybridizing stem region begins to form and fluorescence at the wavelength associated with the FRET fluorescent compound F2 is detected. The high temperature (i.e., melting) probe (labeled HTP) works by incorporating a fluorescent compound and a fluorescence quencher on each of the ends of the self-hybridizing stem region. As the temperature in the tube increases the self-hybridizing stem region begins to separate and fluorescence at the wavelength associated with the fluorescent compound F3 is detected. The L-DNA sequences and associated fluorescent dyes are stable over this entire temperature range and function as they do in the first cycle over a large number of thermal cycles.

Figure 11:
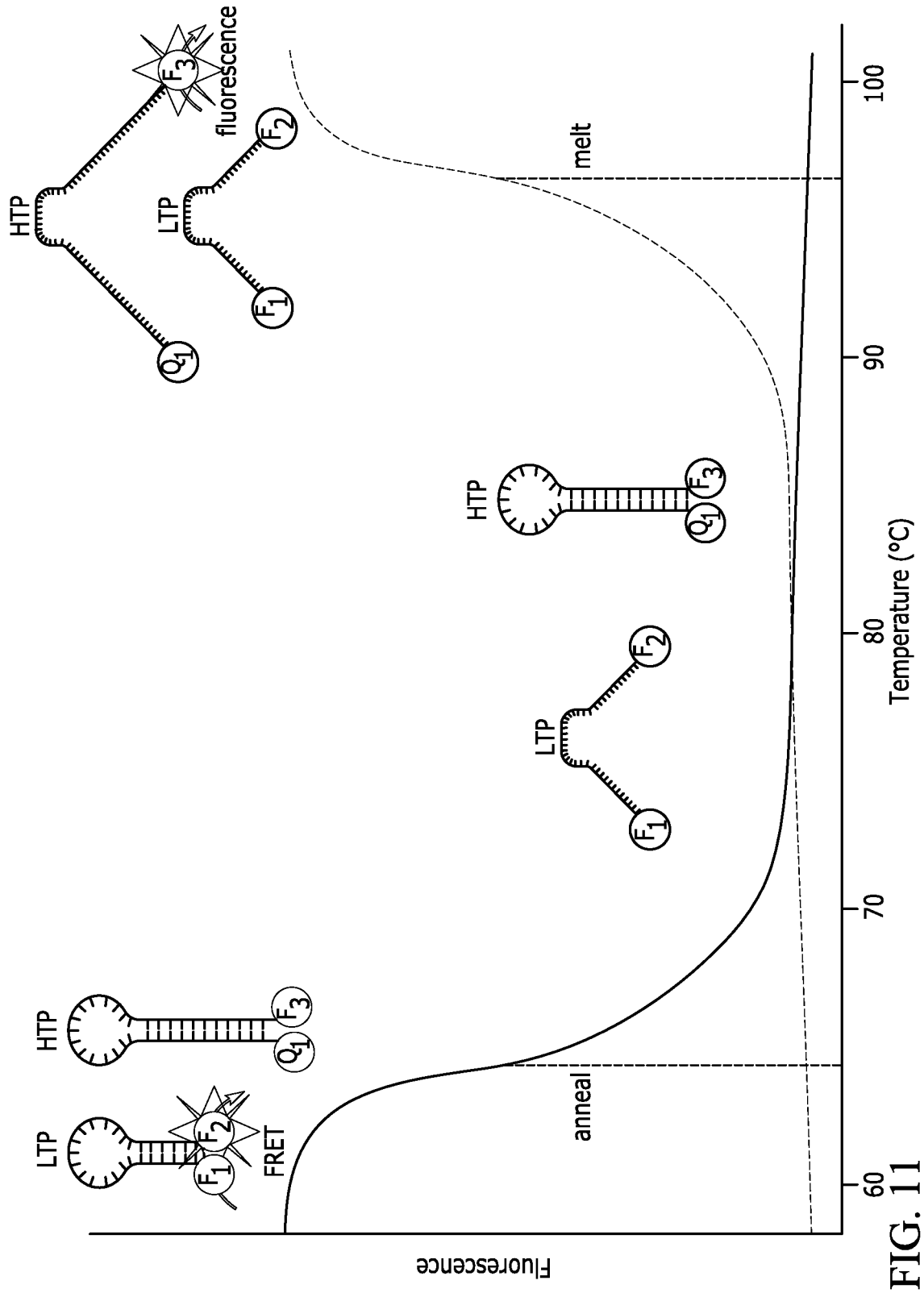
FIG. 11 provides a graph and schematic representation showing how L-DNA hairpin oligonucleotides function as structural sensors during PCR annealing and melting steps.
Figure 12:
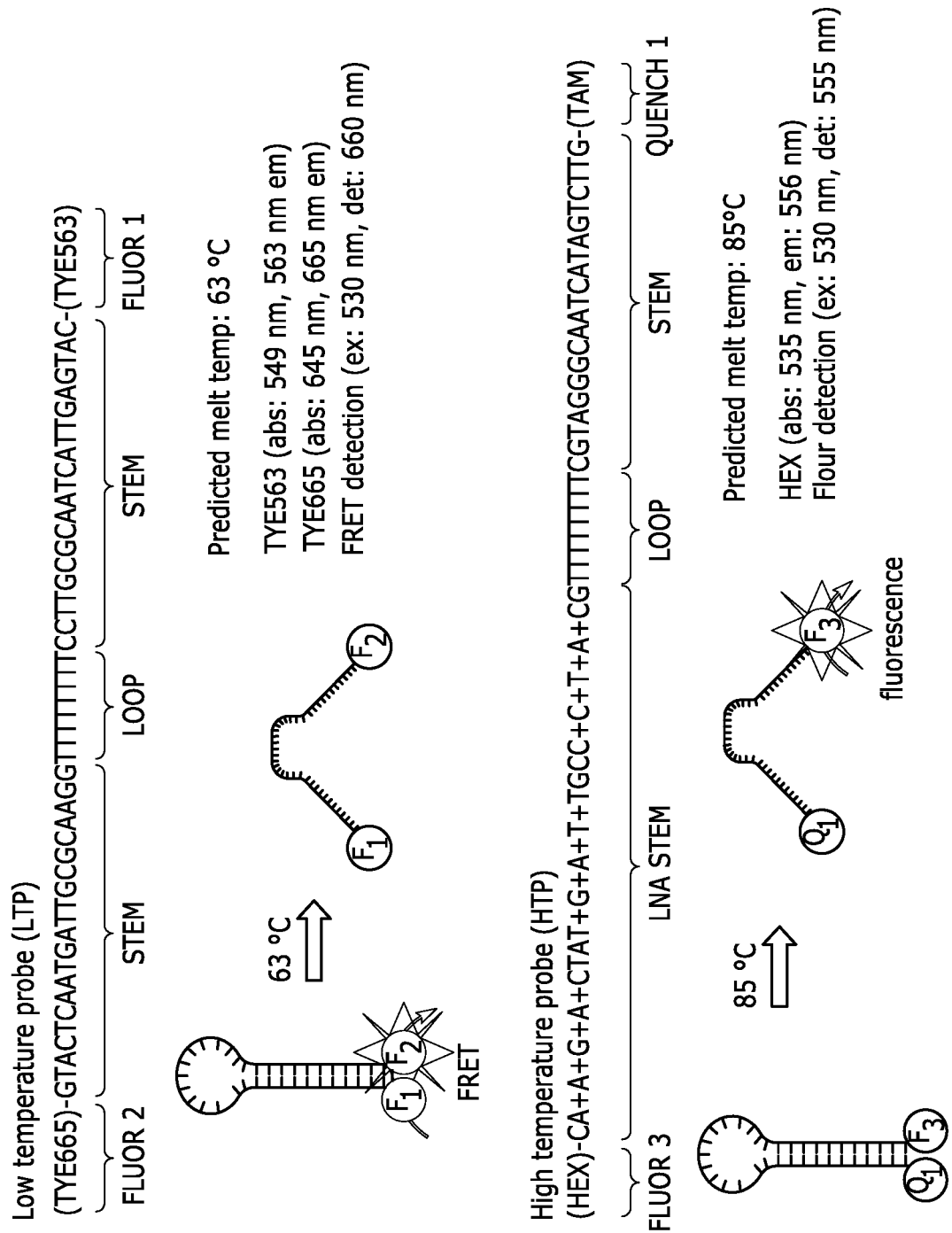
FIG. 12 provides examples of melting and annealing probe sequences using in L-DNA-hairpin studies using a FRET and quencher design. Figure discloses SEQ ID NOS 9-10, respectively, in order of appearance.
Figure 13:
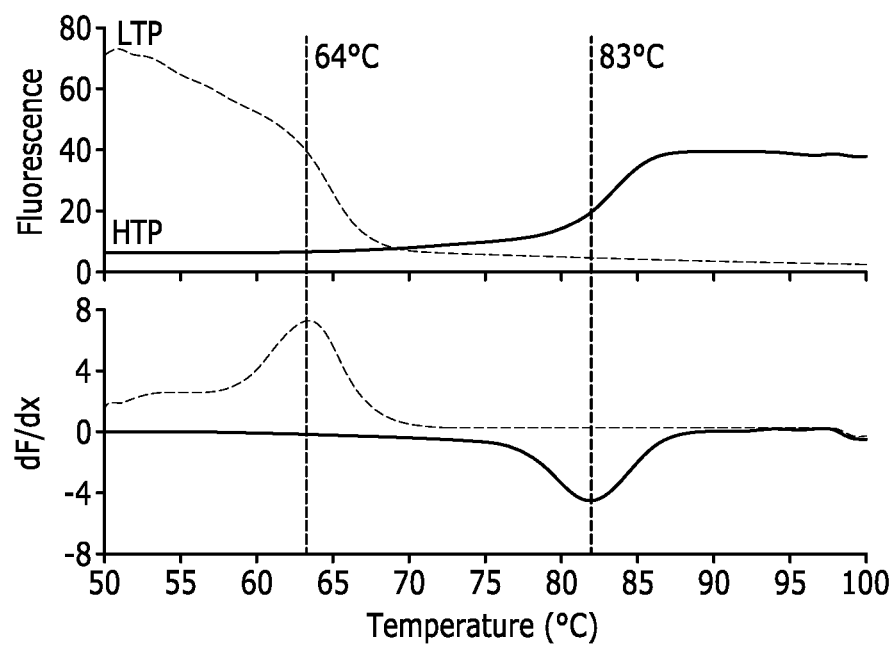
FIG. 13 provides graphs showing that L-DNA hairpin probes function as structural sensors.
Figure 14:
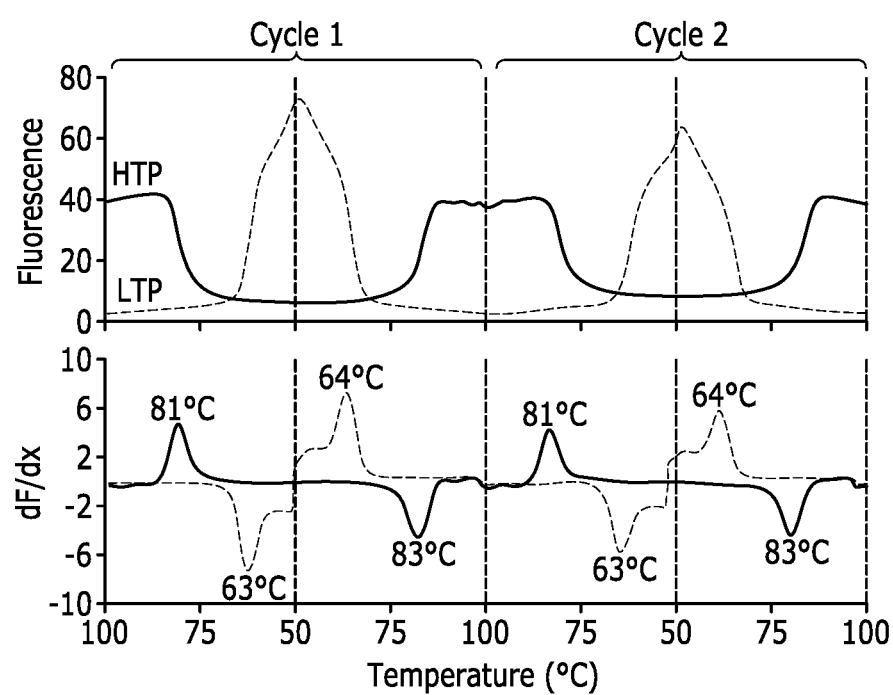
FIG. 14 provides graphs showing that L-DNA hairpin probes generate fluorescence signals during thermocycling corresponding to the annealing and melting steps.

The most accurate estimate of the temperature from the melting and annealing curves shown in the FIG. 11 can be obtained by tracking the change in fluorescence over time. In particular the first derivative of these curves is likely to be the most easily identifiable and accurate estimate of the actual temperature. In this figure these are marked with dotted lines. The strategy of using the derivative of the optical signal is standard practice for determining the melt temperature for anticipated or unknown DNA structures contained in a completed realtime PCR reaction. Typical melt curve analysis employs intercalating dyes such as Sybr green which fluorescence when a double stranded product is present but as the thermal energy in the solution is increased the strands eventually "melt" or move apart, releasing the intercalating dye and decreasing fluorescence. A similar phenomenon occurs in the present method, but instead of characterizing the unknown structure, the method uses additives with known structures to characterize the temperature. Results using these hairpin structures (sequence details for two example probes being provided in FIG. 12) indicate that this design is feasible for temperature sensing during thermal cycling (FIGS. 13 and 14).

These temperature sensing structures could also be designed to produce fluorescence signal at temperatures 1-2° C. higher and lower than the ideal temperature needed for isothermal amplification reactions, such as loop-mediated amplification (LAMP), helicase-dependent amplification (had), cross-primer amplification (CPA), and rolling circle amplification (RCA), which would enable isothermal amplification without the use of thermometer or other thermal sensor. Signal from the lower temperature probe would indicate that the reaction needs to be heated slightly and signal from the high temperature probe would indicate that the reaction needs to be cooled slightly. Using this same approach, three temperature PCR could be enabled. For some PCR samples, an elongation temperature is needed for the polymerase enzyme to function efficiently. Temperature sensing structures could also be designed to produce fluorescence signal at temperatures 1-2° C. higher and lower than the ideal temperature needed for elongation.

Figure 15:
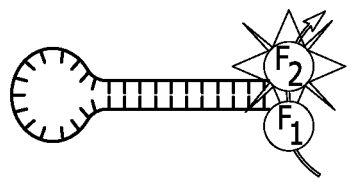
FIG. 15 provides schematic representations of different types of L-DNA probes that can be used to monitor DNA hybridization during various methods such as PCR.
Figure 15:
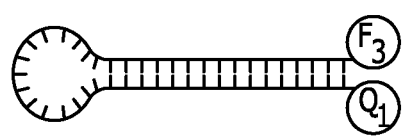
Figure 15:
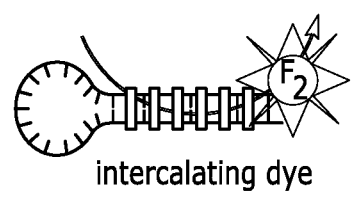
Figure 15:
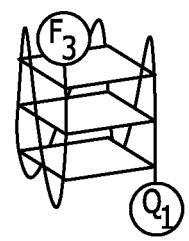
Figure 15:
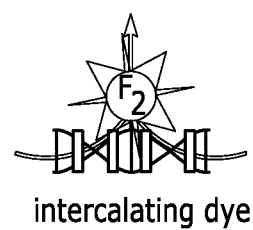
Figure 15:
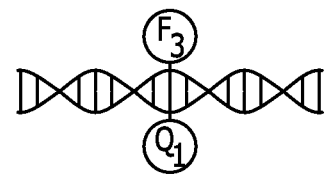

Alternative structures that could be used for annealing and melting probes include DNA, RNA, and locked nucleic acid (LNA) or mixed nucleotide structures, two separate oligonucleotide strands, G-quadruplex structures, or intercalating dyes as FRET donors or acceptors. Some of these structures are illustrated in FIG. 15. It is expected that some of these probes would function similarly to the hairpin probes evaluated in the examples provided herein, but they may offer advantages in compatibility with the oligonucleotides, reaction conditions, or optical sensing capabilities.

Any of the L-DNA probes described herein can be used to monitor thermal cycling. In some embodiments, the annealing L-DNA probe includes a first L-DNA polynucleotide comprising the target polynucleotide and including a first dye component at the end of the first L-DNA polynucleotide and a second L-DNA polynucleotide comprising a the primer polynucleotide and including a second dye component at the complementary end of the second L-DNA polynucleotide, and the melting L-DNA probe includes a third L-DNA polynucleotide having a sequence antisense to the target polynucleotide sequence and including a third dye component at the end of the third L-DNA polynucleotide.

In another embodiment, the annealing L-DNA probe comprises a first polynucleotide consisting of a target polynucleotide region having a first dye component at its 3' end and a primer nucleotide region having a second dye component at its 5' end, with a hinge region between the target polynucleotide region and the primer nucleotide region, capable of forming a hairpin structure, and the melting L-DNA probe comprises a first polynucleotide consisting of a target polynucleotide sequence region having a first dye component at its 3' end and an antisense polynucleotide region having a third dye component at its 5' end, with a hinge region between the target polynucleotide region and the antisense polynucleotide region, capable of forming a hairpin structure.

In a further embodiment, the annealing L-DNA probe comprises a first polynucleotide consisting of a DNA intercalating dye, a target polynucleotide region and a primer nucleotide region, with a hinge region between the target polynucleotide region and the primer nucleotide region, capable of forming a hairpin structure, and the melting L-DNA probe comprises a DNA intercalating dye, a first polynucleotide consisting of a target polynucleotide sequence region and an antisense polynucleotide region, with a hinge region between the target polynucleotide region and the antisense polynucleotide region, capable of forming a hairpin structure.

The DNA being amplified can be obtained from a biological sample. Biological samples include, but are not necessarily limited to bodily fluids such as urine and blood-related samples (e.g., whole blood, serum, plasma, and other blood-derived samples), urine, cerebral spinal fluid, bronchoalveolar lavage, saliva, nasal lavage, breast milk, mucus, and sputum, and the like. Another example of a biological sample is a tissue sample. A biological sample may be fresh or stored (e.g. blood or blood fraction stored in a blood bank). Samples can be stored for varying amounts of time, such as being stored for an hour, a day, a week, a month, or more than a month. The biological sample may be a bodily fluid expressly obtained for the assays of this invention or a bodily fluid obtained for another purpose which can be subsampled for use in the methods of the present invention.

Biological samples are obtained from a subject. As used herein, the term "subject" generally refers to any vertebrate, including, but not limited to a mammal. Examples of mammals including primates, including simians and humans, equines (e.g., horses), canines (e.g., dogs), felines, various domesticated livestock (e.g., ungulates, such as swine, pigs, goats, sheep, and the like), as well as domesticated pets (e.g., cats, hamsters, mice, and guinea pigs).

In some embodiments, the methods of the present invention may can be used for detecting a gene specific to a pathogen. The pathogen is not particularly limited, and specific examples include pathogenic bacteria, pathogenic viruses, food poisoning bacteria, and bacteria and viruses causing hospital infections. More specifically, there may be mentioned, for example, viruses such as hepatitis C virus (HCV), cytomegalovirus (CMV), Epstein-Barr virus (EBV), herpesviruses, and human immunodeficiency virus (HIV); bacteria such as *Escherichia coli* (e.g. O157), *Mycobacterium tuberculosis, Salmonella typhi, salmonella* bacteria, and *Vibrio parahaemolyticus*; and *P. falciparum*, and microorganisms such as *mycoplasma*.

Estimating DNA Amplification Using L-DNA Probes

In another aspect, the method includes estimating the amount of target polynucleotide that has been amplified using target polynucleotide that is fluorescently labeled, and further including the step of determining and comparing the levels of fluorescence of the target polynucleotide and the melting and annealing L-DNA probes to estimating the amount of target polynucleotide that has been formed. This method can be used to estimate the amount of a target polynucleotide prepared by any DNA amplification method, such as PCR.

In using PCR to assay a patient sample for the presence of a particular DNA biomarker fragment, the results obtained from the unknown is compared with a set of standards containing known concentrations of the biomarker. One of the major challenges to implementing this sensing technology to detect small numbers of a biomarker is this need to include multiple parallel reactions for comparison. The inventors have determined that a known concentration of the expected DNA amplicon in L-DNA form along with its sensor pairs can be used as a single point threshold sensor for the formation of product during the PCR reaction as well as verifying the structural homology of the PCR product.

In this application of the present invention, as the PCR reaction proceeds over a number of prescribed cycles the L-DNA present in the sample produces a fluorescent signal on one channel of a detector that is continuously compared to a second fluorescence channel designed to detect the PCR biomarker product that results from the presence of the targeted biomarker. If the sample contains the biomarker of interest, the fluorescence in the second channel begins to increase with PCR cycling and eventually approach and exceed that of the L-DNA monitoring reagents that do not participate in the amplification process. Note that this is because the polymerase only works on right-handed DNA strands and not L-DNA strands. Any fluorescent non-participating spike would perform similarly, but the presence of the L-DNA standard also provides a powerful means to verify the identity of the amplicon produced during the PCR reaction.

Methods of Characterizing Target Polynucleotides Using L-DNA Probes

Another aspect of the invention provides a method of characterizing a target polynucleotide comprising the steps of: (a) providing a sample including a fluorescently labeled target polynucleotide and a primer, (b) adding a melting and/or annealing L-DNA probe including fluorescent dyes having different emission frequencies from the target polynucleotide to the sample, (c) optically exciting the sample. (d) heating the sample to separate the target polynucleotide by melting while generating a fluorescent profile for the target polynucleotide and the melting L-DNA probe, and/or (e) cooling the sample until the target polynucleotide and the primer have annealed while generating a fluorescent profile for the target polynucleotide and the annealing L-DNA probe, and (f) comparing the fluorescent profile of the target polynucleotide with the fluorescent profile of the melting L-DNA probe and/or the annealing L-DNA probe to characterize the identity of the target polynucleotide.

At the point where similar fluorescences (as defined by the assay type) are detected the tube contents are simply subjected to a traditional melt curve analysis, that is a sweep from low to high temperature while recording the fluorescences in both fluorescence channels. In traditional melt curve analysis the absolute temperature at each point of the melting process is critical to determining the identity of the unknown. That is completely unnecessary with this method. The need to know the actual temperature is replaced with the comparison of the melt characteristics of the identical but oppositely folded structure present in the same sample. Identity is confirmed if the variation in fluorescence with temperature variation exactly matches that of the known L-DNA structure.

In some embodiments, the target polynucleotide characterized is the product of a PCR amplification process. L-DNA probes can be used for determining that the correct PCR product was produced in a PCR reaction, without the use of a thermometer or other thermal sensing device. The procedure would include heating or cooling a sample and monitoring the fluorescence profile of the fluorescent dye-labeled L-DNA analog and comparing it to fluorescent profile of the PCR product. The degree to which the fluorescent profiles align is an indication of the accuracy of PCR product. Because intercalating dyes, such as SYBR Green, intercalate in L- and D-DNA forms, a single peak in the melt analysis derivative indicates identical match between the L-DNA probe and PCR product, and two or more peaks indicate a mismatch between the L-DNA probe and the PCR product.

In other embodiments, the method of characterizing a target polynucleotide is used to provide a single nucleotide polymorphism analysis. L-DNA probes to specific DNA sequences of interest could be used for highly sensitive SNP analysis of the respective DNA sequences. The procedure would include heating or cooling a sample and monitoring the fluorescence profile of the fluorescent dye-labeled L-DNA analog and comparing it to fluorescent profile of the DNA sequence of interest. The degree to which the fluorescent profiles align is an indication of the number of mismatched nucleotides in the DNA sequence of interest. The number of mismatched nucleotides could be predicted based on the offset of the two fluorescent profiles.

The following examples are included for purposes of illustration and are not intended to limit the scope of the invention.

EXAMPLES

Figure 16:
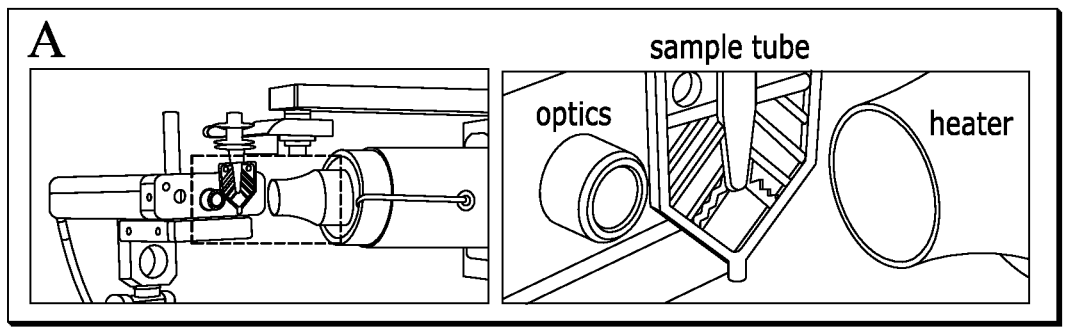
FIGS. 16A-16C provides images showing (A) the current prototype for performing HT-PCR has three major components: 1) optics for monitoring the hybridization state of L-DNA probes and PCR product, 2) a forced-air heater, and 3) software to control heating and cooling based on L-DNA fluorescence profiles and (B) and (C) graphs showing performance of the prototype.
Figure 16:
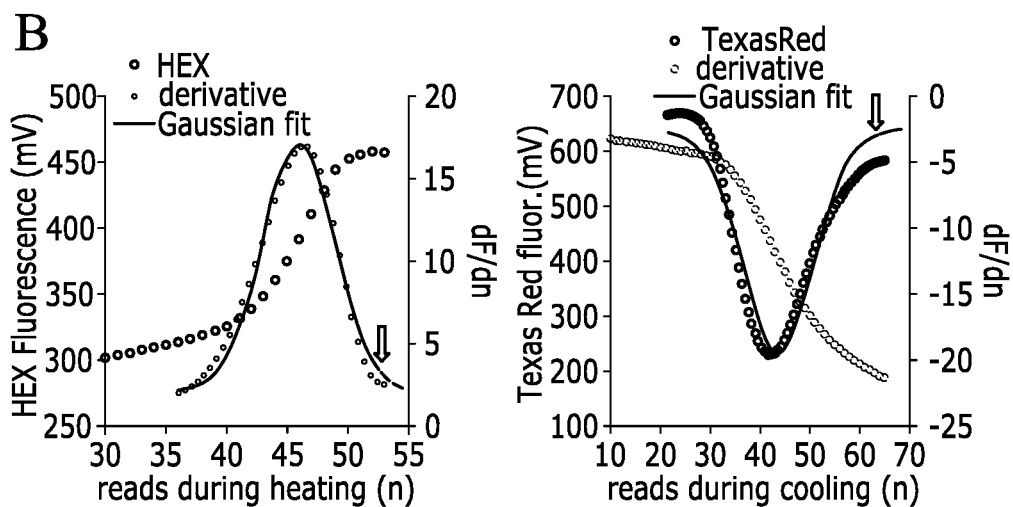
Figure 16:
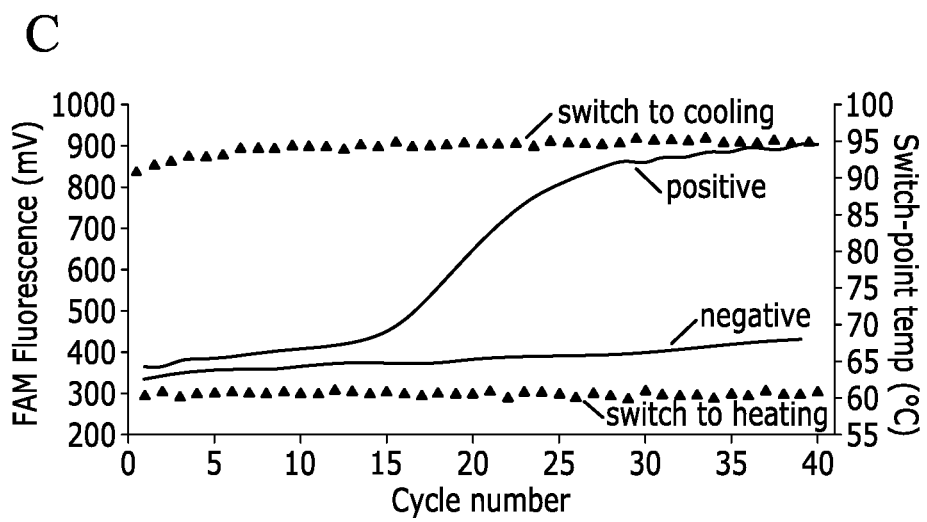

Example 1: Evaluate Performance of HT-PCR Alpha-Prototype Instrument Using the Primer and Hybridization Probe Sequences A prototype of a PCR instrument for use in some aspects of the invention is shown in FIG. 16A, and consists of Qiagen fluorimeters with channels for FAM, HEX, and Texas Red, a hot air source, a removable Cepheid 25 μL reaction tube and some simple electronics interfaced to LabView control software. The heat source is turned on and off in response to L-DNA hybridization events that create concentration-independent characteristic optical signals. The inventors prepared and split a PCR reaction mixture containing the D-DNA primers and the L-DNA reporter sequences. One half of each reaction was run using a RotorGene laboratory instrument and the other half was placed into the Cepheid PCR tube and placed into the prototype. A standard dilution series of template concentrations was run to demonstrate performance. FIG. 16B shows the absolute fluorescence and derivative of the melting L-DNA probe during heating (left panel) and of the annealing L-DNA probe during cooling (right panel). Switch decisions are made based on a fit of the Gaussian distribution to the derivative. FIG. 16C shows the amplification of a DNA product as well as passively acquired melt and annealing temperatures during the run.

Table 1 lists table lists the PCR primer and Tuberculosis target sequences and the L-DNA sequences used in this example (SEQ ID NOS 1-3, 1, and 3-4, respectively, in order of appearance).

| | Description | Sequence (5'-3') |
|---|---|---|
| PCR reagents | Forward PCR primer | ctttgtcaccgacgcccac |
| | Reverse PCR primer | tcgaggaccatggaggtg |
| | PCR hydrolysis probe* | FAM-ctgggctg-Quencher (Roche UPL probe #26, prod. no. 04687574001) |
| | PCR template (sense)# | ctttctcacccacgcctacg tcgcaggatcctgggctggcg ggtcgcttccacgatggccac ttccatggtcctcca |
| L-DNAs | Forward L-DNA primer | TexasRed-atttgtcaccga cgcctac |
| | Sense L-DNA target | HEX-ctttgtcacccacgcct acgtcgcaggatcctgggctg gcgggtcgcttccacgatggc cacctccattgccctcga |
| | Antisense L-DNA target# | tcgaggaccatggaggtggcc accgtggaagcgacctgccag cccaggatcctgcgacgtagg cgtccgtgacaaag-BHQ2 |

*Hydrolysis probe is made of all locked-nucleic acid (LNA) bases.
Primer binding regions are underlined.

Example 2: Evaluate the Temperature Operation Range of HT-PCR

One of the challenges of developing a PCR instrument for non-laboratory settings is that ambient temperatures can fluctuate during the reaction and can be well above 30° C. (86° F.), even indoors. Precise temperature regulation is fundamental to the calibration-dependent design of existing PCR machines. To control thermal cycling, PCR machines generally use thermocouple probes to monitor the temperature of the material surrounding the reaction tube (usually an aluminum block or air). Using these thermal measurements, algorithms estimate the temperature inside of PCR sample tube based on factory calibrations. Because heat transfer does not scale linearly with the thermal gradient in complex systems and because measurement errors are disproportionately propagated at higher and lower temperatures, the thermal calibrations of PCR machines are only valid within a relatively narrow range of ambient temperatures. For example, Qiagen RotorGene Q and Roche LightCycler instruments have an operating range of 18-30° C. and Cepheid GeneXpert operates within 15-30° C.

Figure 17:
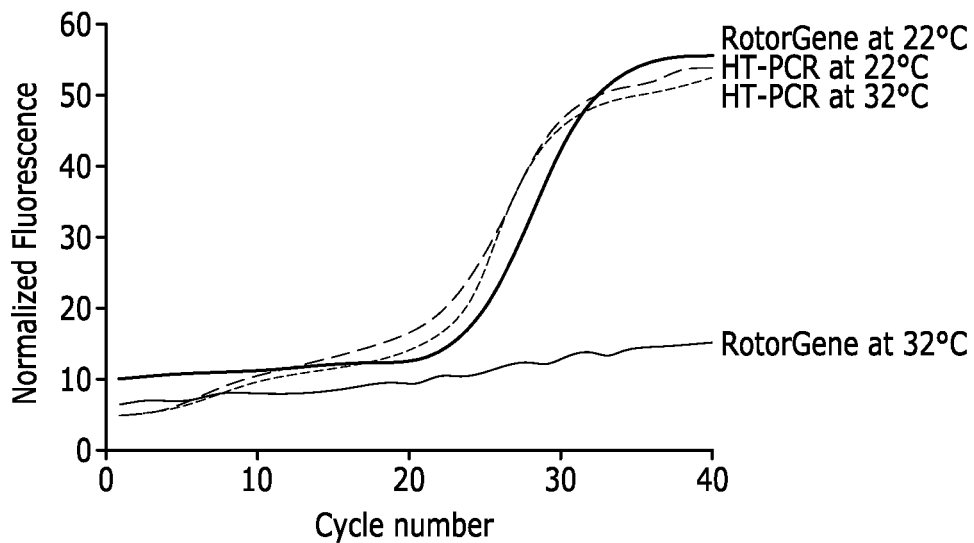
FIG. 17 provides a graph showing that HT-PCR performed similarly at room temperature and elevated temperature. The Qiagen RotorGene Q instrument performed similarly to HT-PCR at room temperature, but failed at elevated temperatures.

Because HT-PCR is not dependent on predictive algorithms and estimated temperatures, the operational temperature range and tolerance to temperature fluctuations is much greater than traditional PCR. The inventors demonstrated this by comparing performance of their HT-PCR prototype to a commercial RT-PCR machine in a storage room heated to 32° C. (max temp allowed). The data suggest that HT-PCR performs well over this range of temperatures, while the commercial RT-PCR machine failed at high temperatures (FIG. 17). The inventors also tested the HT-PCR instrument at temperatures up to 40° C. to test the effects of temperature changes during the reaction. This was done by placing the prototype instrument in a storage room heated in 5° C. graduations from 10 to 40° C., then evaluating the efficiency of amplification. PCR efficiency was determined based on statistical delimitation of fluorescence increase during the exponential phase of the amplification curve as described by Tichopad et al. Tichopad et al., Nucleic acids research 31, e122 (2003).

Example 3: Evaluate Corrective Response to Variation in the Chemical Composition of the Reaction Another challenge with implementing PCR in point-of-care settings is the inability to predict what ends up in the PCR sample. Molecules and chemicals known to inhibit PCR fall into a few categories: those that cleave or degrade biomolecules (e.g., proteases, nucleases), those that block or reduce the efficiency of polymerase (e.g., $Fe^{2+}$, heme), and those that change the hybridization properties of DNA (e.g., salts, alcohols, sugars). Removing these chemical and molecules is the basis for most solid-phase and two-phase DNA extraction methods. However, chemicals from the sample preparation buffers such as salts and ethanol are commonly inadvertently carried into the PCR reaction (Sur et al., The Journal of molecular diagnostics: JMD 12, 620-628 (2010)) and change the hybridization properties of nucleic acids. Alternative sample preparation reagents have been developed for performing PCR directly in patient samples (i.e., urine and blood) by diluting and blocking PCR inhibitors (Aggarwal et al., Indian journal of orthopaedics 46, 531-535 (2012)), but these methods do not control for or regulate the patient-to-patient variation in the salt concentrations in the samples. Because PCR is optimized by adjusting salt levels (namely, magnesium) to tune the primer hybridization properties, the result of introducing unknown amounts of salts and ethanol is that the primers do not anneal at the expected temperatures.

Figure 18:
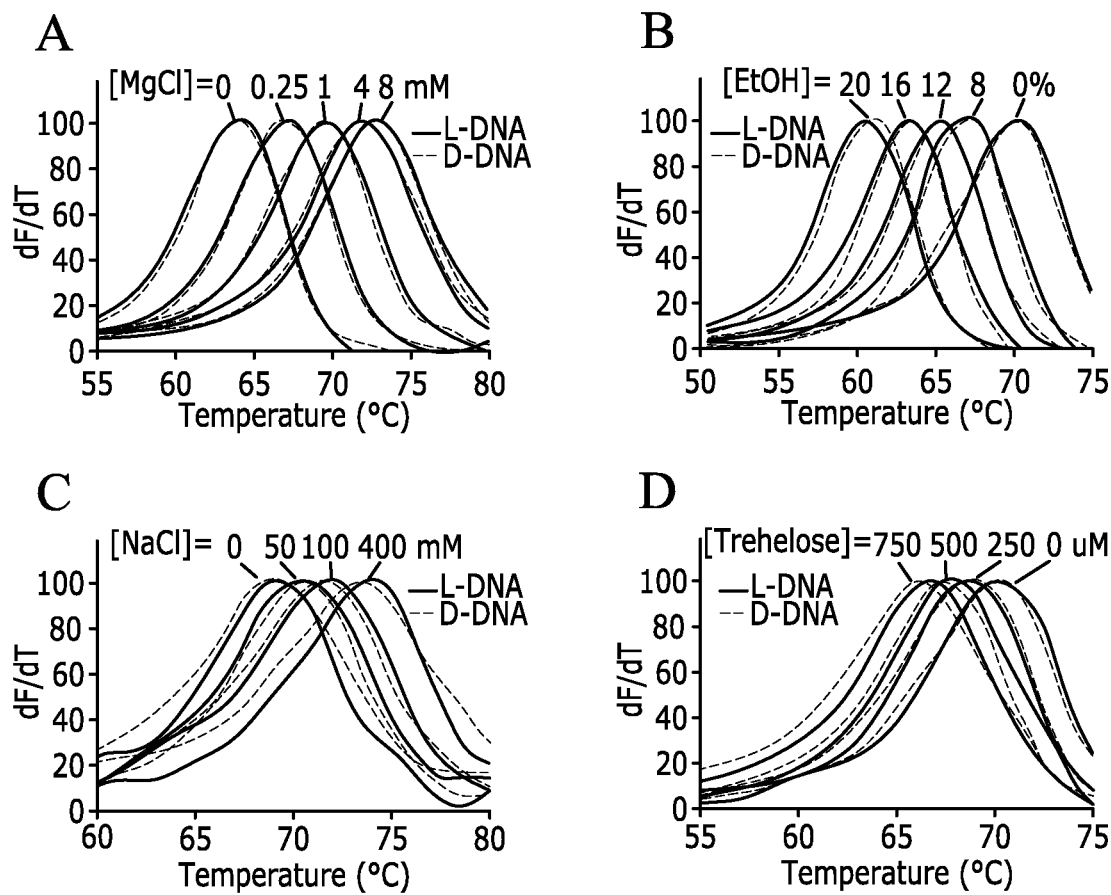
FIGS. 18A-18D provide graphs showing L-DNA primer annealing response to (A) $Mg^{2+}$, (B)ethanol, (C) sodium chloride, and (D) trehelose concentration is identical to D-DNAs using hybridization melt analysis. L-DNAs (solid line) and D-DNAs (dotted line) were prepared in PCR buffer containing 0, 1, and 3 mM $Mg^{2+}$ ((A), left to right) and fluorescence was monitored as the temperature was increased. Similar concentration changes for (B), (C), and (D) are shown in figure labels.
Figure 19:
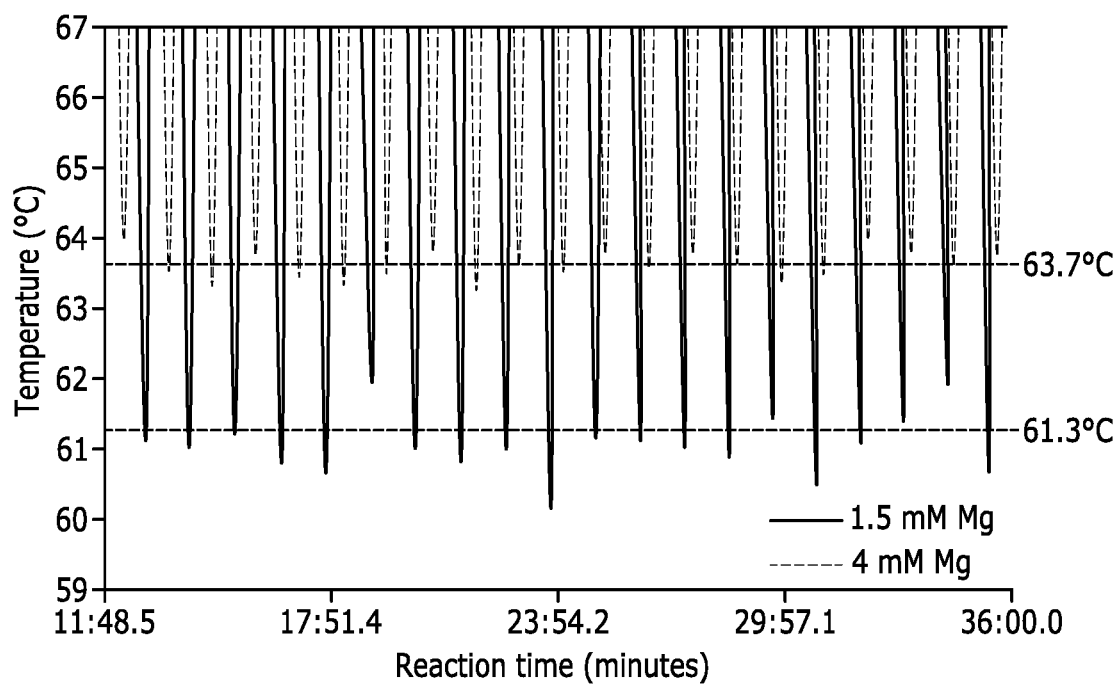
FIG. 19 provides a graph showing the "self-calibration" response to $Mg^{2+}$ during 20 HT-PCR cycles. Passive temperature measurements were collected using 1.5 mM $Mg^{2+}$ and 4 mM $Mg^{2+}$ in the PCR reaction mix. The switch point for annealing was ~61.3° C. for 1.5 mM $Mg^{2+}$ and 63.7° C. for 4 mM $Mg^{2+}$. Note: The graph is scaled for annealing and does not show full cycle temperatures.

Because HT-PCR directly monitors the hybridization state of the primers and products in the PCR reaction, the method auto-correct for the effects of these hybridization-altering PCR variants. To demonstrate this, the inventors have shown that L-DNA anneal temperature is affected identically to D-DNA with increasing $Mg^{2+}$ concentrations (FIG. 18). Our preliminary data also demonstrates that direct hybridization monitoring corrects for hybridization changes produced by the presence of $Mg^{2+}$ and trehelose sugar in a PCR reaction (FIGS. 18 and 19). The goal of this objective is to determine the sample preparation design limits for interferents introduced into the sample during the sample preparation step. In addition, these results are particularly useful for informing the design of the constraints for the sample preparation kit reagents. The limits of the self-calibrating characteristics of the HT-PCR approach was evaluated using additives to the PCR reaction. PCR samples were prepared with common PCR interferents and conditions present in sample preparation protocols that can be carried into PCR reactions and are known to impact nucleic acid hybridization, including $Na^+$, $K^+$, $Mg^{2+}$, trehelose, guanidinium thiocyanate, ethanol, and pH. The effect of these chemical variants and conditions on nucleic acid hybridization were determined using concentrations that might be expected in diluted patient samples, in samples prepared from DNA extraction methods, or in rehydrated lyophilized samples (i.e., 0-100 mM of $Na^+$, 0-100 mM of $K^+$, 0-4 mM of $Mg^{2+}$, 0-5 mM of EDTA, 0-100 mM guanidinium thiocyanate, 0-5% ethanol, and 5-9 pH @ 25° C.). Melt and anneal temperatures of the D-DNA and L-DNA amplicons and primers were evaluated in each of these conditions to validate that the response of L-DNA matches that of the D-DNA. Next, the amplification efficiency of reactions containing these interferents were evaluated using traditional temperature-based thermal cycling and L-DNA-based thermal cycling. The approach was then evaluated using surrogate patient samples of TB, P. falciparum and E. coli spiked into their biological matrices as previously described. Bitting et al., "Automated Device for Asynchronous Extraction of RNA, DNA, or Protein Biomarkers from Surrogate Patient Samples," Journal of laboratory automation (2015) Epub. The results should demonstrate no statistical difference (P<0.05) in PCR efficiency between the baseline HT-PCR and parallel reactions containing 2.5±2 mM $Mg^{2+}$, 50±25 mM $K^+$, 10±10 mM $Na^+$, 8.3±0.5 pH, 0-3% ethanol, or performed at 15-40° C. ambient temperature.

Figure 20:
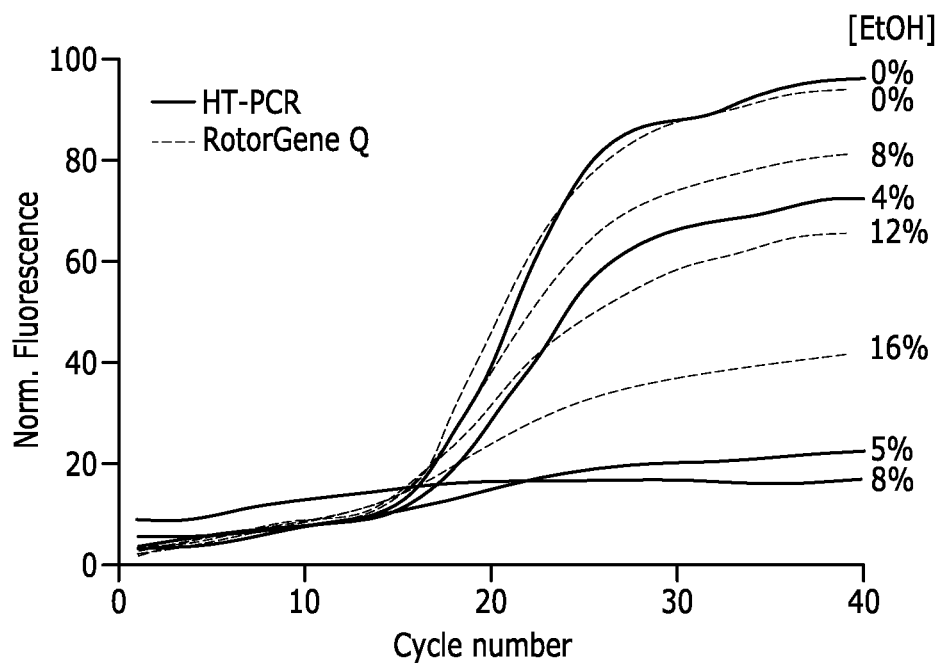
FIG. 20 provides a graph showing that HT-PCR is tolerant of up to 12-16% ethanol, while the traditionally designed Qiagen RotorGene Q instrument failed with >4% ethanol.

An additional example advantages of HT-PCR for correcting for chemicals is provided in FIG. 20, which shows that HT-PCR is tolerant of up to 12-16% ethanol.

Example 4: Design and Evaluate Primer and Hybridization Probe Sequences for TB, P. falciparum, and E. coli In this example, the inventors will use standard molecular biology tools to screen candidate PCR primer and hybridization probe designs using BLAST secondary structure analysis for each disease target. The following three major steps for tuberculosis, P. falciparum, and E. coli DNA targets will be followed. First, selection and optimization of PCR primer pairs. Primers and probes will be chosen from sequences developed by the inventors, vetted by the CDC, described in highly cited sources, or designed using third-party software. In addition, current L-DNA synthesis constraints limit candidate amplicons to <200 nucleotide bases. Novel candidate sequences will be picked using the NCBI Primer-BLAST software tool to ensure each candidate PCR primer pair will be specific for the organism selected. Each candidate sequence will be evaluated by RT-PCR on a BioRad CFX 96, for primer efficiency and specificity. Gel electrophoresis will be performed on each reaction to visually verify PCR results. Second, selection and optimization of D-DNA candidate amplicon hybridization probe sets. Candidate amplicon hybridization probe sets will initially be screened using D-DNA sequences. Based on the inventors results using on the optical design shown in FIG. 3, for each candidate amplicon hybridization probe set they will synthesize: i) an amplicon strand with 3' BHQ2, ii) a complement amplicon strand with 5' HEX and iii) primer with 5' Texas Red. These dyes were chosen because they are compatible with the FAM dyes used for PCR amplification and they show little fluorescence variance between 60 and 100° C. Third, synthesis of L-DNA amplicon hybridization probes sets. After evaluation of the D-DNA, the inventors will synthesize L-DNA versions of the best performing amplicon hybridization probe sets. Cross-reactivity of the L-DNA and D-DNA will then be evaluated by mixing combinations of the L-DNAs and the D-DNAs to determine if there is any cross-hybridization between strands. A Bio-Rad CFX96 thermal cycler will be to verify that the anneal and melt responses align with the target PCR amplicons and primers.

Example 5: A Rapid and Robust HT-PCR Instrument

At the point-of-care, the time-to-result requirement of a diagnostic tests varies depending on setting, but the general goal is to obtain a diagnostic result while the patient is waiting so that treatment can occur within the same visit. The amount of time that is reasonable for a patient to wait is debatable, but there seems to be a general consensus that 30 minutes from sample collection to diagnostic outcome is ideal, which aligns with the Bill & Melinda Gates Foundation's target product profile (TPP) for a panel of diagnostic tests for *P. falciparum*, *M. tuberculosis*, and *E. coli*. Given that sample preparation is expected to take ~10 minutes, a 20 minute HT-PCR test time would be preferred, which given 40 cycles of PCR, corresponding to a 30 second cycle time. Interestingly, PCR cycling is not limited by the rate of primer annealing, dNTP diffusion, or enzyme turnover, which occurs on the order of milliseconds, but it is generally limited by the 'thermal inertia' of the heated components of the system and the precision at which the temperatures can be achieved given the temperature sensing lag during rapid cycling. Sanford, L., and Wittwer, C., Journal of Molecular Diagnostics 14, 743-743 (2012). In the inventors' design, thermal inertia is minimized by isolating the PCR sample tube as the only heated component and using forced-air heater in place of a heated aluminum block. Using a HT-PCR prototype with the addition of a cooling fan, the inventors have demonstrated that their system is capable of cycling between 95 and 60° C. in about 25 seconds per full cycle. Because the inventors rely on direct monitoring of primer and product hybridization rather than temperature, issues related to temperature sensing lag are overcome. The optical sampling rate is the current limiting feature for the PCR cycle length of the prototype HT-PCR design.

In the HT-PCR prototype, the cycle switch decision is made using the derivative of the smoothed fluorescence curves of the L-DNA interactions, which resembles a Gaussian curve (see FIG. 16B). Because the data is analyzed in real-time, a Gaussian fit is made using fluorescence values as they are acquired. The area under the Gaussian curve is interpreted as the number of amplicons melted (during heating) or annealed primers (during cooling), which allows the software to switch between heating or cooling based on the number of primers annealed or products melted. The Qiagen ESE log fluorimeters used in the current prototype are currently set up to read approximately 1.3 times per second, which results in a 90 second cycle (60 minutes for 40 cycles). To ensure minimal error at the switch point (<0.5° C.), an optical sampling rate of <5 reads per second is required. This is because an average heat ramp rate and cooling rate of 2.3° C./second to achieve the 30 second cycle time required for 20 minute PCR (2.3° C./s÷0.5° C.=4.6 reads/s). We expect to achieve this higher optical sampling by modifying the read cycle of the current optics or obtaining optics with continuous fluorescence feedback.

Example 6: HT-PCR Software

Figure 21:
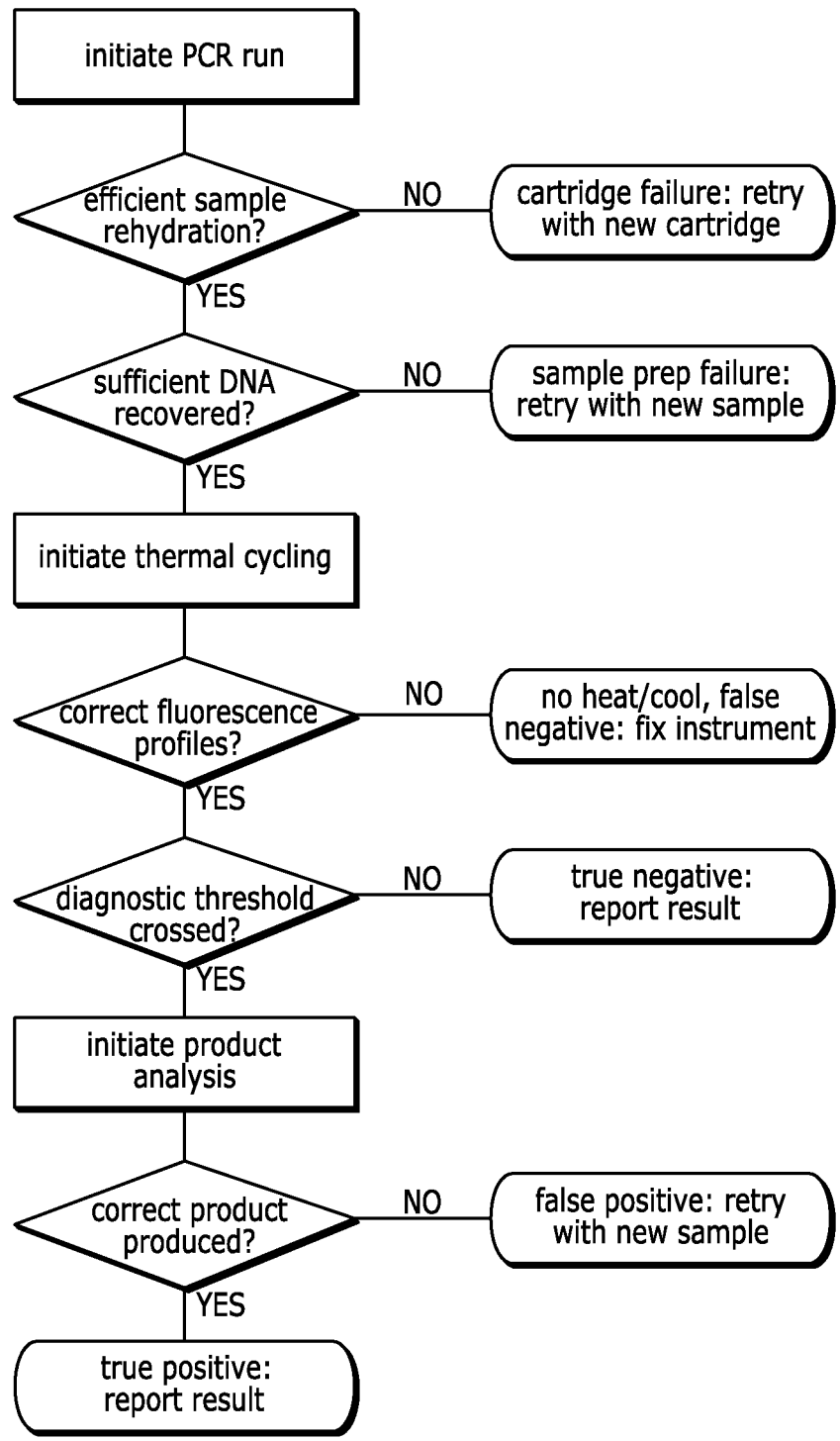
FIG. 21 provides a scheme showing a proposed automated software decision tree based on L-DNA-enabled controls for single-tube HT-PCR. After the initiation of a process (rectangles), the software makes decisions (diamonds) based on optical inputs from the fluorescently-labeled L-DNAs and PCR product. Based on the outcomes of the decisions, the software progresses through the program or generate prompts for the operator (ovals).

Modifications to existing software will be made to interpret additional developed controls and to simplify the interface for off-site use. The goal of this objective is to develop software that not only is simple for the end-user to use, but that provides the user feedback on the status of the PCR process. The software will be gated to progress through the PCR process only when certain criteria are met (FIG. 21). For example, in the first step after initiating a PCR run, the device will check for fluorescence values of the rehydrated probes, to ensure that the sample was rehydrated correctly. This automation is exploited to guarantee success even with the varied abilities of different operators, and the varied quality of the stored reagents.

Software changes will be incorporated in the main LabVIEW control program to interpret the controls included within the reagent kit. The proposed software decision tree for incorporating these controls is shown in FIG. 21. All of these are designed to make the single tube implementation more specific, but they are not all of equal priority. Choices will be made to achieve the highest level of performance required but that do not significantly impact the overall cost of the instrument or reagents as well as their effect on overall simplicity of operation and interpretation. As a final software package, the LabVIEW program will be compiled as an executable that the end-user cannot edit or change. The simple interface will allow the user to start and abort a run, view the progress through the process, and view the outcomes of the run. The instrument will collect other data, such as the fluorescence curves of the hybridization probes, the PCR curve, and other instrument information, to be accessed by the developers for interpreting device operation. The modified instrument and cartridge should achieve an amplification efficiency of >90% and within ≤20 minutes (30 second cycle time).

Example 7: Effectiveness of Different L-DNA Probes

To better understand a demonstrate the response of such sensing probes the following experimental examples including sensor compositions and response or sensing activity of such sensing probes are provided.

TABLE 2

PROBES PROVIDED IN THE FOLLOWING EXPERIMENTS:

| NAME | NUCLEOTIDE SEQ 5'-3' |
|---|---|
| THERMO FWD62 | TACATCCGTGAGGTGAATGTG (SEQ ID NO: 5) |
| THERMO 62REV COMPL | CACATTCACCTCACGGATGTA (SEQ ID NO: 6) |
| THERMO FWD69 | TACATCCGTGAGGTGAATGTGGTGAAGT (SEQ ID NO: 7) |
| THERMO REVCMPL69 | ACTTCACCACATTCACCTCACGGATGTA (SEQ ID NO: 8) |
| THERMO 62REV COMPL | CACATTCACCTCACGGATGTA/3IAbRQSp/ (SEQ ID NO: 5) |
| THERMO FWD69 TYE563 | /5TYE563/TACATCCGTGAGGTGAATGTGGTGAAGT (SEQ ID NO: 7) |
| THERMO REVCMPL69 | ACTTCACCACATTCACCTCACGGATGTA/3IAbRQSp/ (SEQ ID NO: 8) |
| THERMO62 C18 TYE563 | /5TYE563/TACATCCGTGAGGTGAATGTG/iSp18/CACATTCACCTCACGGATGTA/3IAbRQSp/ (SEQ ID NOS 5-6, respectively, in order of appearance) |
| THERMO69 C18 TYE563 | /5TYE563/TACATCCGTGAGGTGAATGTGGTGAAGT/iSp18/ACTTCACCACATTCACCTCACGGATGTA/3IAbRQSp/ (SEQ ID NOS 7-8, respectively, in order of appearance) |
| THERMO62_C3 | /5TYE563/TACATCCGTGAGGTGAATGTG/iSpC3/CACATTCACCTCACGGATGTA/3IAbRQSp/ (SEQ ID NOS 5-6, respectively, in order of appearance) |
| THERMO69_C3 | /5TYE563/TACATCCGTGAGGTGAATGTGGTGAAGT/iSpC3/ACTTCACCACATTCACCTCACGGATGTA/3IAbRQSp/ (SEQ ID NOS 7-8, respectively, in order of appearance) |

TABLE 2-continued

PROBES PROVIDED IN THE FOLLOWING EXPERIMENTS:

| NAME | NUCLEOTIDE SEQ 5'-3' |
|---|---|
| THERMO62_C9 | /5TYE563/TACATCCGTGAGGTGAATGTG/iSp9/CACATTCACCTCACGGATGTA/3IAbRQSp/ (SEQ ID NOS 5-6, respectively, in order of appearance) |
| THERMO69_C9 | /5TYE563/TACATCCGTGAGGTGAATGTGGTGAAGT/iSp9/ACTTCACCACATTCACCTCACGGATGTA/3IAbRQSp/ (SEQ ID NOS: 7-8, respectively, in order of appearance) |

Experiment 1

Purpose: Probes purchased from (IDT) Integrated DNA Technologies, Coralville, Iowa, with different linkers connecting the complementary strands each with Dye TYE 563 on the 5' end and quencher AbRQSp on the 3' end, to evaluate of the effect of linkers on the overall melting temperature of the probes.
1. Thermo62_C3-(TYE563)21mer FWD/C3 linker/21mer REV(AbRQSp) diluted to 100 pMole/µl in 0.1×TE, 2% Acetonitrile.
2. Thermo62_C9-(TYE563)21mer FWD/C9 linker/21mer REV(AbRQSp) diluted to 100 pMole/µl in 0.1×TE, 2% Acetonitrile.
3. Thermo62_C18-(TYE563)21mer FWD/C18 linker/21mer REV(AbRQSp) diluted to 100 pMole/µl in 0.1×TE, 2% Acetonitrile.
4. Thermo69_C18-(TYE563)28mer FWD/C18 linker/28mer REV(AbRQSp) diluted to 100 pMole/µl in 0.1×TE, 2% Acetonitrile.

Figure 22:
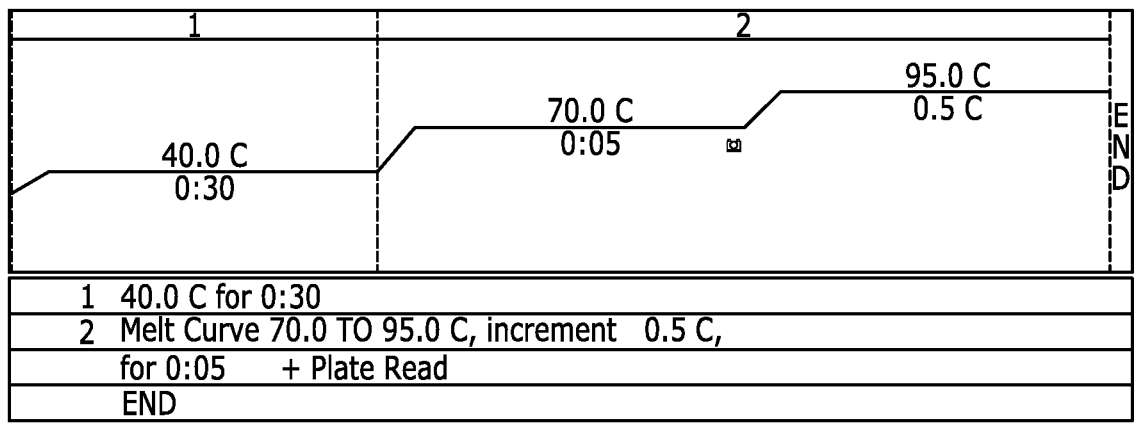
FIGS. 22A-22C provide graphs showing the effect of different linkers on melting temperature. (A) shows the run data. (B) shows the melt curve. (C) shows the melt peaks, where BThermo62_C3=84.5° C., Thermo62_C9=84.5° C., Thermo62_C18=86° C., and Thermo69_C18=86° C.
Figure 22:
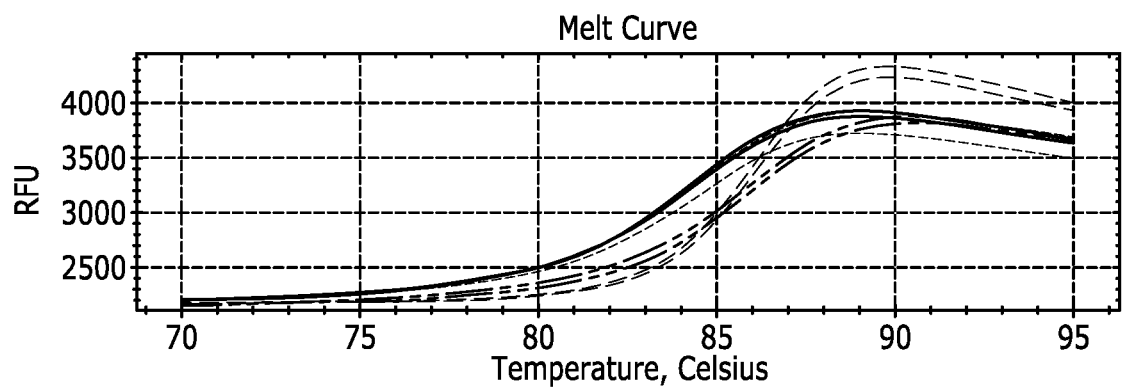
Figure 22:
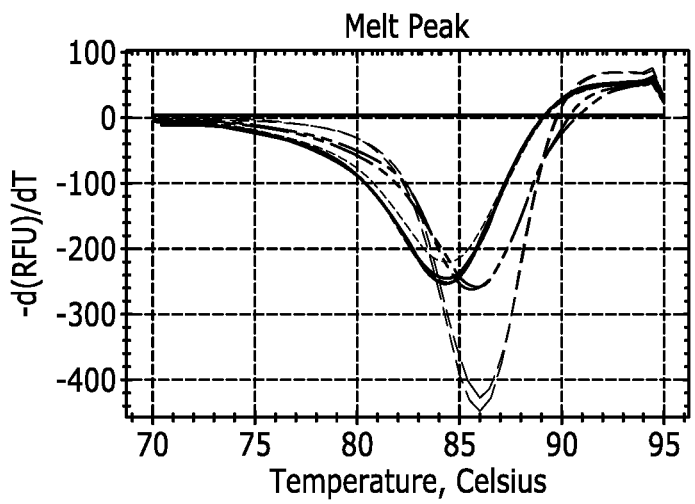

For each of the above probes a 1:200 dilution was made with 10 mM Tris HCl pH 9.0, 50 mM KCl, 0.1% Triton-X (1×PCR buffer) with 2.0 mM $MgCl_2$ by adding 398 µl of 1× PCR buffer and then 2 µl of appropriate probe. Samples were added to a white 0.2 mL strip tube (BioRad catalog #TLS-0851) by adding 20 µl of dilution in duplicate, an optical clear cap was attached and the strip was added to BioRad (2000 Alfred Nobel Drive, Hercules, Calif. 94547) CFX96 Real-Time System in column 3 and an empty balance strip was added to column 10. Samples were processed by running program 70_95MELT. See FIG. 22A. A melt curve was obtained, as in FIG. 22B. FIG. 22C shows the melt peaks.

Results: Complementary 21mer probes with the C3 linker and the C9 linker had identical melting peaks of 84.5° C. The complementary 21mer probes with the C18 linker and the complementary 28mer probes with the C18 linker also had an identical melting peak of 86° C. This observation was much different than the predicted melting temperature of 67.3° C. for the complementary 21 mer probe and 69° C. for the complementary 28mer probe.

Experiment 2

Purpose: To further investigate the effect of the linker on the melting temperature of the probes the inventors evaluated probes with no linker. The following probes were evaluated:
1. ThermoFWD62_TYE 563 diluted to 100 pMole/µl in 0.1×TE, 2% Acetonitrile.
2. ThermoREV62_AbRQSp diluted to 100 pMole/µl in 0.1×TE, 2% Acetonitrile.
3. ThermoFWD69_TYE 563 diluted to 100 pMole/µl in 0.1×TE, 2% Acetonitrile.
4. ThermoREV69_AbRQSp diluted to 100 pMole/µl in 0.1×TE, 2% Acetonitrile.

Figure 23:
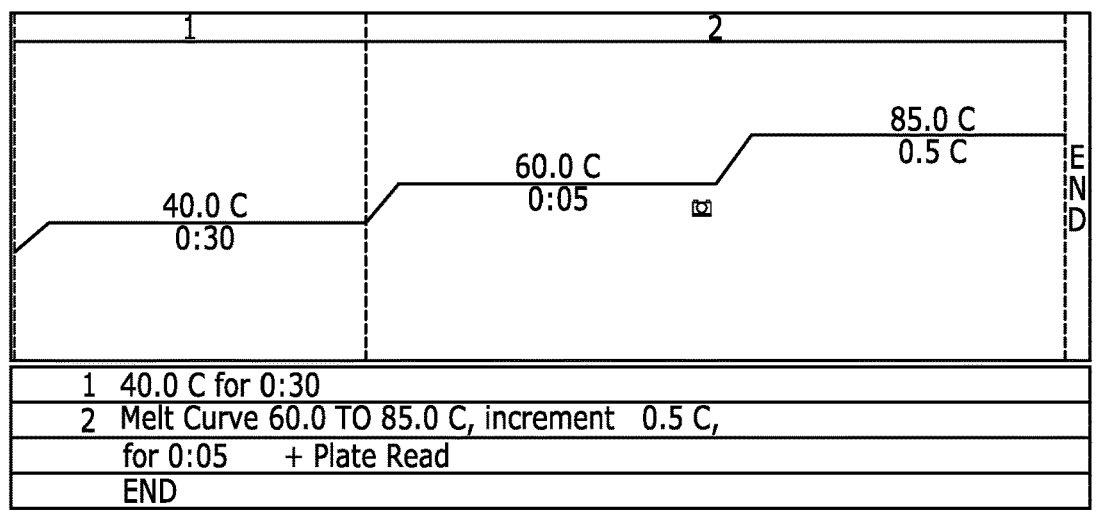
FIGS. 23A-23C provide graphs showing the effect of the absence of linkers on melting temperature. (A) shows the run data. (B) shows the melt curve. (C) shows the melt peaks, where Themo62_FWD_dye563/REV_Quench=71.5° C.; and Thermo69_FWD_dye563/REV_Quench=75.5° C.
Figure 23:
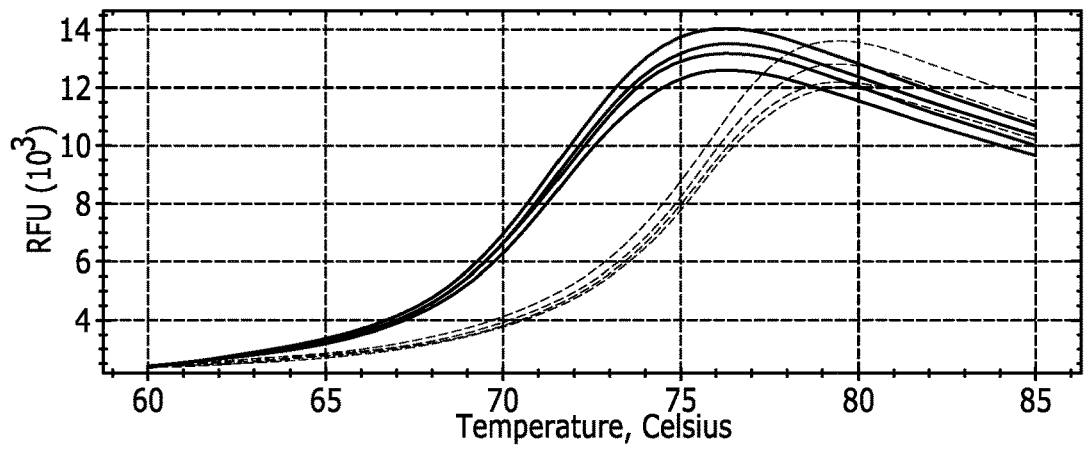
Figure 23:
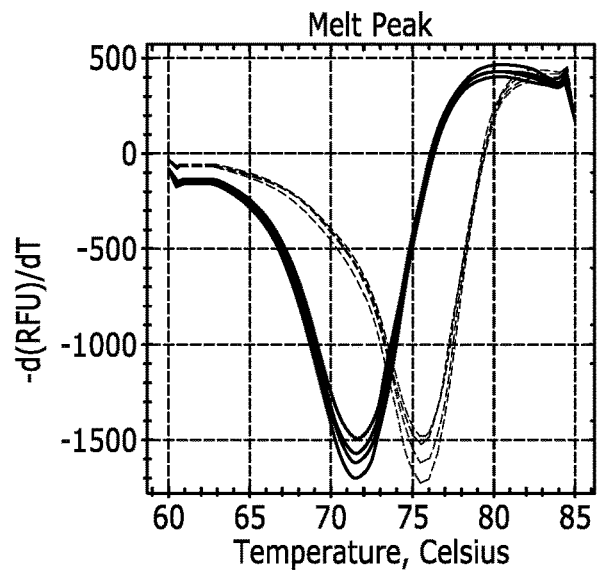

Diluted the FWD probes 1:100 by combining 1 µl of Probe and 99 µl of 1×PCR buffer 2.0 mM $MgCl_2$ and the REV probes 1:50 by combining 2 µl of probe and 98 µl of 1× PCR buffer 2.0 mM $MgCl_2$. Combined 10 µl of 1 and 2 for 1:200 of Dye and 1:100 of Quencher added to first four wells of 0.2 mL white strip tubes. Combined 10 µl of 3 and 4 for 1:200 of Dye and 1:100 of Quencher in the bottom four wells of the strip tube. Made sure that the probes were annealed by running thermo_aneal program: denature at 95° C. for 2 min, cool to 60° C. for one minute, cool to room temp, end. Then ran 60_85MELT on BioRad CFX96 Real-Time System. See FIG. 23A. A melt curve was obtained, as shown in FIG. 23B. FIG. 23C shows the melt peaks.

Results: The absence of the linker has a dramatic effect on the melting temperature of the probe. The melting temperature of the Thermo62 went from 84.5° C. (C3, C9) and 86° C. (C18) with the linker to 71.5° C. without and Thermo69 went from 86° C. with the linker to 75.5° C. without.

Experiment 3

Purpose: To evaluate if removing the dye and the quencher changes the melting temperature if the probe. Evaluated the following unlabeled probes with no linker:
1. ThermoFWD62_unlabeled diluted to 100 pMole/µl in 0.1×TE, 2% Acetonitrile.
2. ThermoREV62_unlabeled diluted to 100 pMole/µl in 0.1×TE, 2% Acetonitrile.
3. ThermoFWD69_unlabeled diluted to 100 pMole/µl in 0.1×TE, 2% Acetonitrile.
4. ThermoREV69_unlabeled diluted to 100 pMole/µl in 0.1×TE, 2% Acetonitrile.

Figure 24:
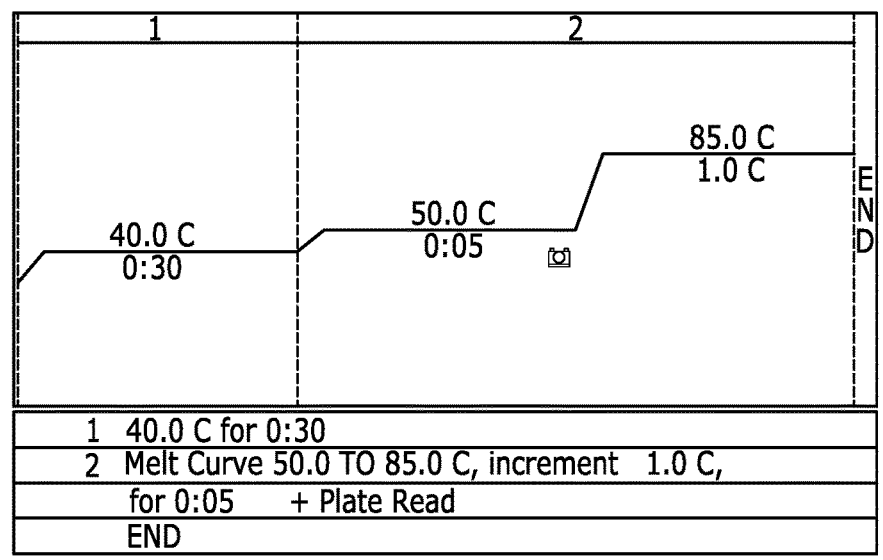
Figure 24:
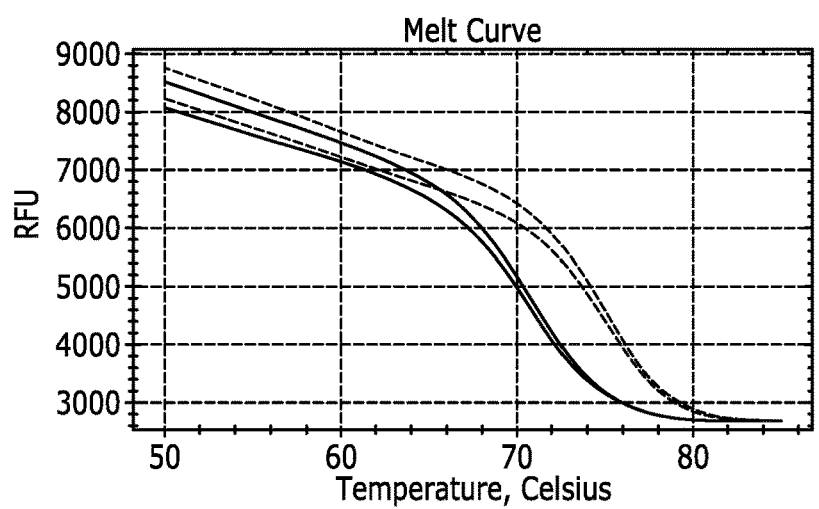
Figure 24:
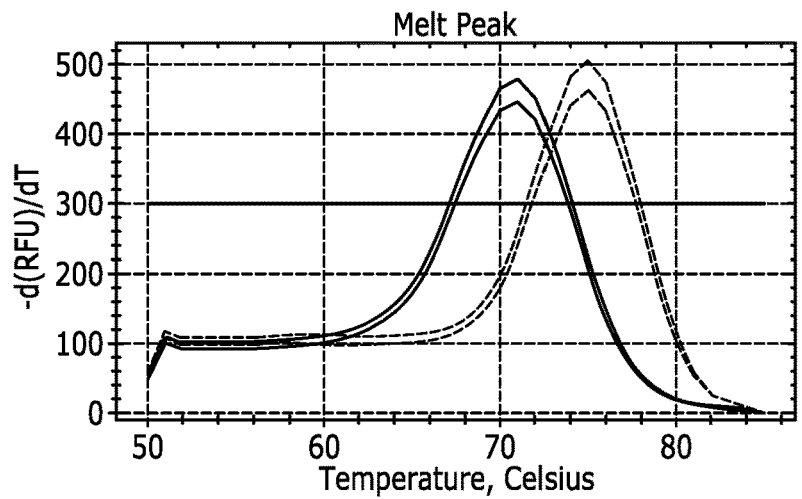

Diluted the FWD probes 1:100 by combining 1 µl of Probe and 99 µl of 1×PCR buffer 2.0 mM $MgCl_2$ 0.1×SYBR and the REV probes 1:50 by combining 2 µl of probe and 98 µl of 1×PCR buffer 2.0 mM $MgCl_2$ 0.1×SYBR. Combined 10 µl of 1 and 2 for 1:200 dilution of FWD and 1:100 dilution of REV, added in duplicate to wells of 0.2 mL white strip tubes. Combined 10 µl of 3 and 4 for 1:200 dilution of FWD and 1:100 dilution of REV in duplicate to wells of the strip tube. Made sure that the probes were annealed by running thermo_aneal program: denature at 95° C. for 2 min, cool to 60° C. for one minute, cool to room temp, end. Then ran 50_85MELT on BioRad CFX96 Real-Time System. See FIG. 24A. A melt curve was obtained, as shown in FIG. 24B. FIG. 24C shows the melt peaks.

Results: The removal of the dye and quencher do not have a significant effect on the melting temperature of the probe. Melting temperature of the Thermo62 was 71.5° C. with the dye/Quencher and 71° C. without and the Thermo69 had a melting peak of 75.5° C. with the dye/quencher and 75° C. without.

CONCLUSION

Surprisingly the addition of a carbon linker in between two complementary strands of DNA has a large effect on the melting temperature of that probe. The net effect is increasing the melting temperature in the range of 10.5° C. to 14.5° C. when compared to the same probe sequence without the linker attached.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A system for performing a polymerase chain reaction (PCR) and monitoring the reaction during temperature cycling using L-DNA, comprising:
   a sample container comprising a PCR sample including a target D-DNA polynucleotide, a primer D-DNA polynucleotide, a melting L-DNA probe wherein the melting L-DNA probe comprises a fluorescent dye, and an annealing L-DNA probe wherein the annealing L-DNA probe comprises a fluorescent dye,
   wherein the annealing L-DNA probe comprises a first L-DNA polynucleotide consisting of a first region and a second region wherein the first region comprises the identical sequence to a target D-DNA polynucleotide sequence region having a first dye component at its 3' end and wherein the second region comprises the identical sequence to a primer D-DNA polynucleotide sequence region having a second dye component at its 5' end, with a hinge region between the first region and the second region, capable of forming a hairpin structure, and wherein the melting L-DNA probe comprises a second L-DNA polynucleotide consisting of a third region and a fourth region wherein the third region comprises the identical sequence to a target D-DNA polynucleotide sequence region having a first fluorescent dye component at its 3' end and wherein the fourth region comprises a sequence antisense to the target polynucleotide sequence region having a second fluorescent dye component at its 5' end, with a hinge region between the third region and the fourth region, capable of forming a hairpin structure, a heat exchange component for heating and cooling the PCR sample, a control device for repeatedly operating the heat exchange component to subject the PCR sample to thermal cycling, an excitation source for optically exciting the PCR sample to detect the fluorescence of the melting and annealing L-DNA probes, a photodetector configured for detecting fluorescent emission from the melting and annealing L-DNA probes producing fluorescence data signals, and a processor configured to receive fluorescence data signals from the photodetector and process the signals to control the heat exchanger using the control device.

2. The system of claim 1, wherein the hinge region of the melting and annealing L-DNA probes consists of an alkyl hydrocarbon or polyethylene glycol chain.

3. The system of claim 1, wherein the hinge region of the melting and annealing L-DNA probes consists of an alkyl hydrocarbon or polyethylene glycol chain.

4. The system of claim 1, wherein the melting and annealing L-DNA probes have a size of from 15 to 200 nucleotides.

5. A system for performing a polymerase chain reaction (PCR) and monitoring the reaction during temperature annealing using L-DNA comprising A sample container comprising a PCR sample wherein the PCR sample comprises a target D-DNA polynucleotide, a primer D-DNA polynucleotide, a melting L-DNA probe, and an annealing L-DNA probe, wherein the annealing L-DNA probe comprises a first L-DNA polynucleotide comprising the identical sequence to the target D-DNA polynucleotide sequence and a first fluorescent dye compartment at the 3' or 5' end of the first L-DNA polynucleotide and a second L-DNA polynucleotide comprising the identical sequence to the primer D-DNA polynucleotide sequence and a second fluorescent dye component at the 5' or 3' end, respectively, of the second L-DNA polynucleotide, and wherein the melting L-DNA probe comprises a third L-DNA polynucleotide comprising the antisense strand to the target polynucleotide sequence and a third fluorescent dye component at the 5' or 3' end of the third L-DNA polynucleotide, a heat exchange component for heaving or cooling the PCR sample, a control device for repeatedly operating the heat exchange component to subject the PCR sample to thermal cycling, an excitation source for optically exciting the PCR sample to detect the fluorescence of the melting and annealing L-DNA probes, a photodetector configured for detecting fluorescent emission from the melting and annealing L-DNA probes producing fluorescence data signals, and a processor configured to receive fluorescence data signals from the photodetector and process the signals to control the heat exchanger using the control device.

6. The system of claim 5, wherein the melting and annealing L-DNA probes have a size of from 15 to 200 nucleotides.

* * * * *